US012697566B2

(12) United States Patent
Conner et al.

(10) Patent No.: US 12,697,566 B2
(45) Date of Patent: Aug. 4, 2026

(54) PARALLEL CHROMATOGRAPHY SYSTEMS AND METHODS

(71) Applicant: AMGEN INC., Thousand Oaks, CA (US)

(72) Inventors: Jeremy S. Conner, Newbury Park, CA (US); Glenn M. Hunter, Thousand Oaks, CA (US); Kenneth Shoemaker, Thousand Oaks, CA (US); Neil Soice, Simi Valley, CA (US); Bret Wylie, Thousand Oaks, CA (US); John B. Flynn, Thousand Oaks, CA (US); Nakorn Kaeonil, Thousand Oaks, CA (US); Thuy N. Nguyen, Thousand Oaks, CA (US); Siddharth Singh, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 407 days.

(21) Appl. No.: 18/268,683

(22) PCT Filed: Feb. 17, 2022

(86) PCT No.: PCT/US2022/016685
§ 371 (c)(1),
(2) Date: Jun. 21, 2023

(87) PCT Pub. No.: WO2022/191971
PCT Pub. Date: Sep. 15, 2022

(65) Prior Publication Data
US 2024/0075406 A1　　Mar. 7, 2024

Related U.S. Application Data

(60) Provisional application No. 63/159,176, filed on Mar. 10, 2021.

(51) Int. Cl.
　　*B01D 15/18*　　(2006.01)
　　*C07K 1/16*　　(2006.01)

(52) U.S. Cl.
　　CPC ............ *B01D 15/1885* (2013.01); *C07K 1/16* (2013.01)

(58) Field of Classification Search
　　CPC ........ B01D 15/1885; C07K 1/16; C07K 1/18; C07K 1/22; C07K 1/36
　　See application file for complete search history.

(56) References Cited

U.S. PATENT DOCUMENTS

| | | | |
|---|---|---|---|
| 2002/0020670 A1 | 2/2002 | Petro | |
| 2014/0255994 A1* | 9/2014 | Konstantinov | ...... B01D 15/327 |
| | | | 435/69.6 |

(Continued)

FOREIGN PATENT DOCUMENTS

| | | |
|---|---|---|
| CN | 103842045 A | 6/2014 |
| CN | 105980847 A | 9/2016 |
| CN | 112433009 A | 3/2021 |
| EP | 3 683 231 A1 | 7/2020 |

(Continued)

OTHER PUBLICATIONS

Mihlbachler, Integrated Downstream Processing: An Enabling Manufacturing Approach, LEWA Process Technologies, Inc. (2015).

(Continued)

*Primary Examiner* — Waqaas Ali
(74) *Attorney, Agent, or Firm* — MARSHALL, GERSTEIN & BORUN LLP

(57) ABSTRACT

Parallel chromatography systems and continuous manufacturing methods are described herein that utilize two or more chromatography column skids having columns operating in parallel with automation controls governing which column to load at a given time.

20 Claims, 8 Drawing Sheets

(56)  References Cited

U.S. PATENT DOCUMENTS

| | | | |
|---|---|---|---|
| 2020/0001203 A1 | 1/2020 | Sichting et al. | |
| 2020/0141912 A1* | 5/2020 | Blom | G01N 30/42 |

FOREIGN PATENT DOCUMENTS

| | | | |
|---|---|---|---|
| EP | 3 739 333 A1 | 11/2020 | |
| JP | 2020508857 A | 3/2020 | |
| WO | WO-0168216 A2 * | 9/2001 | B01D 15/1885 |
| WO | WO-2013050104 A1 | 4/2013 | |
| WO | WO-2015121425 A1 | 8/2015 | |
| WO | WO-2019001778 A1 * | 1/2019 | G01N 30/88 |
| WO | WO-2021/046443 A1 | 3/2021 | |

OTHER PUBLICATIONS

International Search Report for Application No. PCT/US2022/016685 dated May 24, 2022.

Written Opinion for Application No. PCT/US2022/016685 dated May 24, 2022.

Coffman et al., "A common framework for integrated and continuous biomanufacturing", PHCBI, Biotechnology and Bioengineering, pp. 1735-1749, Jan. 12, 2021.

Chinese Patent Application No. 202280019842.4, Office Action, dated Jan. 28, 2026.

Chinese Patent Application No. 202280019842.4, Office Action, dated May 14, 2026.

* cited by examiner

300

700

704 Depth Filter Train

712 Viral Filter 716 728 726 730 732

724 714 720 Column Valve 722

External Pressure Sensor

708 AEX

710 CEX

718

702 NVIP

706 Surge Vessel

System Pressure

Inlet A3

UV 734

Post or Pre C Pressure

NVIP Load

736 Outlet Valve to Collection

Effect of Elution Buffer pH and Pool Volume on ProA Pool pH
(36g/Lr, 100mM Formate)

Pool pH

Pool Volume (CV)

- 100mM Formate pH 3.6
- 100mM Formate pH 3.4
- 100mM Formate pH 3.2
- Confirmation Test

PARALLEL CHROMATOGRAPHY SYSTEMS AND METHODS

CROSS-REFERENCE TO RELATED APPLICATION

This is the United States national phase of International Patent Application No. PCT/US22/16685, filed Feb. 17, 2022, which claims priority to U.S. Provisional Patent Application No. 63/159,176, filed Mar. 10, 2021, the entire contents of each of which are hereby incorporated by reference herein.

FIELD OF THE DISCLOSURE

The present disclosure generally relates to chromatography systems and, more particularly, to semi-continuous and continuous manufacturing chromatography systems.

BACKGROUND

Continuous Manufacturing (CM), particularly continuous purification operations, is a goal for many biomanufacturing processes with more than one column chromatography operation. With traditional chromatography operations, a complete batch is processed in multiple cycles on a single large chromatography column, typically greater than 12,000 L with a column diameter greater than 1 meter. Processing on a single large scale chromatography column and collecting the entire product mass in pool tanks prior to the next batch operation increases processing time and the duration of the process, requires a relatively large, less flexible facility footprint, has higher costs for chromatographic materials, such as Protein A, and has greater volumes of buffers and other reagents, which contribute to increased overall cost and can have a greater environmental impact.

To overcome these challenges, various complex multi-column cycling strategies for chromatography operations have been developed to provide a more continuous output of material, thereby improving resin utilization and providing some improvement to impurity resolution. One such method, the closed loop simulated moving bed multi-column system, requires complex configurations of valves, and sophisticated control strategies to achieve process benefits. Another multi-column strategy developed for continuous manufacturing is sequential multi-column chromatography, an example of which is periodic counter-current chromatography (PCC), which employs multiple columns connected in series utilizing column overloading in flow-through configurations between the columns, essentially separating the batch chromatography into smaller units that are processed in a connected, sequential manner.

One difference between these multi-column setups compared to a traditional large scale single column setup is that the resin material can be more fully loaded by overloading a first column and, any non-binding protein in the feedstock breaks through and flows to the next column connected in series. The overloaded column can be eluted and regenerated while the next connected column is overloaded. However, these setups are complex and costly to operate, requiring numerous and complex interconnections between the columns and valving systems to direct fluid flow from one connected column to the next, as well as additional ultraviolet (UV) monitors, and pumps and converters to monitor and process this continuous serial flow. In a larger scale biopharmaceutical manufacturing operation, these complexities can decrease process robustness, cleaning efficiency, and limit adoption of single-use technologies. For example, configuration of a PCC process within a single unit operation leads to inefficient utilization of capital equipment and a loss of flexibility compared to traditional single column chromatography unit operations, especially for the adoption of equipment enabling single-use flowpaths.

Fault tolerance is also an issue for connected multi-column systems, and most particularly where two or more unit operations have been interconnected and contained within a single skid. The interconnection of these components and flow paths can have a significant impact on unit operations and the manufacturing process as a whole. When any component of this interconnected system is impacted, the entire unit operation(s) can be brought to a stop and the entire run up to that point can be lost.

The invention described herein overcomes these deficiencies by defining a mode of operation whereby the equipment and software configuration is smaller scale, platform-friendly, and modularized, the units operated in parallel rather than in a serial configuration, resulting in a system that is flexible, expandable, operated by external control, and not requiring complex set up and flow of material. Additionally, the described system displays superior fault tolerance compared to multi-column serial units, in that if a single unit is unable to function, only the single column is impacted and can be easily isolated and extracted, without the entire run being lost and/or brought to a stop.

SUMMARY

In accordance with a first aspect, a continuous parallel chromatography system is described herein that includes a plurality of chromatography column skids, where each chromatography column skid is suitable for independent batch processing.

Each chromatography column skid includes a chromatography column, an inlet selectively coupled to an upstream source, at least one pump, at least one filter, and an outlet sensor. The system further includes a control circuit configured to control the operation of the plurality of chromatography column skids through one or more full cycles of a chromatography process, where each full cycle includes a long step and a plurality of shorter steps, each of the plurality of shorter steps having a processing time shorter than or equal to a processing time of the long step. The control circuit is configured to receive a synchronization signal associated with a first one of the plurality of chromatography column skids that the long step is complete and, in response to reception of the synchronization signal, direct operation of a second one of the plurality of chromatography column skids to commence operation of the long step.

In some forms, the control circuit can be configured to direct operation of the plurality of shorter steps on the first one of the plurality of chromatography column skids to complete the full cycle of the chromatography process therefor after reception of the synchronization signal. In these forms, the control circuit can further be configured to receive a second synchronization signal associated with the second one of the plurality of chromatography column skids that the long step is complete and, in response to reception of the second synchronization signal, direct operation of the first one of the plurality of chromatography column skids to commence a second operation of the long step. In yet further forms, the control circuit can be configured to direct operation of the plurality of shorter steps on the second one of the plurality of chromatography column skids to complete the full cycle of the chromatography process therefor after reception of the second synchronization signal.

In any of the above forms, the long step can be an eluting step for the chromatography column, where the plurality of shorter steps can include two or more of: an equilibration step, a loading step, one or more washing steps, a regeneration step, or a flushing step and/or the long step can be a loading step for the chromatography column, where the plurality of shorter steps can include two or more of: an equilibration step, one or more washing steps, an elution step, a regeneration step, or a flushing step. In forms having the long step being a loading step, the first one of the plurality of chromatography column skids can be configured to receive a feed of feedstock from the upstream source and send the synchronization signal to the control circuit indicating that a load of the feedstock in the chromatography column of the first one of the plurality of chromatography columns is complete and, in response to reception of the synchronization signal, the control circuit is configured to switch the feed of the feedstock from the upstream source to the second one of the plurality of chromatography column skids to perform the loading step for the chromatography column thereof. In these forms, the control circuit can be configured to direct a feed of one or more processing feedstocks to the first one of the plurality of chromatography column skids to perform processing of the short steps on the loaded chromatography column thereof and, if desired, after completion of the processing of the short steps on the loaded chromatography column, the first one of the plurality of chromatography column skids can be configured to await a generation of a second synchronization signal associated with the second chromatography column skid that the loading step for the chromatography column thereof is complete. In any of these forms, the feedstock can be a protein, an antibody, a multispecific protein, a bispecific protein, or a bi-specific T cell engager and/or the upstream source of the feedstock can be one of: a stream or pool of harvested cell culture fluid, an elution stream or pool from a capture chromatography column, a viral inactivated pool from a capture chromatography column, or a neutralized viral inactivated pool from a capture chromatography column.

In any of the above forms, the chromatography columns of the plurality of chromatography skids can be capture chromatography columns. The capture chromatography columns can be one or more of: affinity chromatography columns, size exclusion chromatography columns, ion exchange chromatography columns, hydrophobic interaction chromatography columns, multi-modal chromatography columns, hydroxyapatite chromatography columns, or immobilized metal affinity chromatography columns. The capture chromatography columns can be affinity chromatography columns consisting of Protein A chromatography columns, Protein G chromatography columns, or Protein L chromatography columns. The capture chromatography columns can be ion exchange chromatography columns consisting of cation exchange chromatography columns or anion exchange chromatography columns.

In any of the above forms, the system can include at least one of a viral filtration device and/or an ultrafiltration device fluidly connected downstream of the plurality of chromatography column skids; the control circuit can be a plurality of controllers of each of the plurality of chromatography column skids in communication with one another or a central controller in communication with each of the plurality of chromatography column skids; the chromatography columns of the plurality of chromatography column skids can have a plurality of different sizes relative to one another; or one or more of the chromatography columns of the plurality of chromatography column skids can be single-use chromatography columns.

In any of the above forms, the system can include one or more collection tanks fluidly coupled downstream of the plurality of chromatography column skids and/or a downstream capture chromatography column. In some forms, the downstream chromatography column can be an ion exchange chromatography column, a hydrophobic interaction chromatography column, a multi-modal chromatography column, or a hydroxyapatite chromatography column. The downstream chromatography column can be a cation exchange or anion exchange column. In further forms, the downstream chromatography column can be a first downstream chromatography column and the system can include a second downstream chromatography column connected directly in series with the first downstream chromatography column, where the first and second downstream chromatography columns can be cation and/or anion exchange columns. In other forms, the downstream chromatography column can be a first downstream chromatography column and the system can further include a second downstream chromatography column, where the first and second downstream chromatography columns are disposed on first and second downstream chromatography column skids, respectively, and the first and second downstream chromatography column skids are each suitable for independent batch processing and an inlet, at least one pump, at least one filter, and an outlet sensor. In these forms, the control circuit can be configured to control operation of the first and second downstream chromatography column skids through one or more full cycles of a downstream chromatography process, each full cycle including a long elution step and a plurality of shorter steps, each of the plurality of shorter steps having a processing time shorter than or equal to a processing time of the long elution step, and to: receive a synchronization signal associated with the first downstream chromatography column skid that the long elution step is complete and, in response to reception of the synchronization signal, direct operation of the second chromatography column skid to commence operation of the long elution step.

In accordance with a second aspect, a method for purification of a recombinant protein from one or more contaminants is described that includes subjecting the protein to an affinity chromatography unit operation, subjecting the elution pool from the affinity chromatography unit operation to low pH viral inactivation and neutralization, and subjecting the neutralized pool to one or more polishing chromatography unit operations. At least one of the affinity chromatography unit operation or at least one of the one or more polish chromatography unit operations are operated according to a parallel chromatography process configured to control the operation of a plurality of chromatography column skids through one or more full cycles of a chromatography process, where each full cycle includes a long step and a plurality of shorter steps and each of the plurality of shorter steps has a processing time shorter than or equal to a processing time of the long step. The parallel chromatography process includes the steps of: receiving a synchronization signal associated with a first one of the plurality of chromatography column skids that the long step is complete at a control circuit of a parallel chromatography system and in response to reception of the synchronization signal, directing operation with the control circuit of a second one of the plurality of chromatography column skids to commence operation of the long step.

In some forms, the affinity chromatography unit operation is performed according to the parallel chromatography process and, in further forms, the long step can be loading a column of the chromatography column skids and the plurality of shorter steps can be two or more of: an equilibration step, one or more washing steps, an elution step, a regeneration step, or a flushing step. In other forms, at least one of the one or more polish chromatography unit operations can be performed according to the parallel chromatography process and, in further forms, the long step can be eluting a column of the chromatography column skids and the plurality of shorter steps can be two or more of: an equilibration step, a loading step, one or more washing steps, a regeneration step, and a flushing step. In yet further forms, both the affinity chromatography unit operation and at least one of the one or more polish chromatography unit operations can be performed according to the parallel chromatography process.

In some forms, the parallel chromatography process can include the step of directing operation of the plurality of shorter steps on the first one of the plurality of chromatography column skids with the control circuit to complete the full cycle of the chromatography process therefor after reception of the synchronization signal and, in further forms, the parallel chromatography process can include the steps of: receiving a second synchronization signal associated with the second one of the plurality of chromatography column skids at the control circuit that the long step is complete and, in response to reception of the second synchronization signal, directing operation of the first one of the plurality of chromatography column skids with the control circuit to commence a second operation of the long step.

In some forms, the method can include one or more of the following: at least one of the one or more polish chromatography unit operations can include first and second polish chromatography unit operations with a first capture chromatography column connected in series with a second capture chromatography column; the one or more polish chromatography unit operations can include separate first and second polish chromatography unit operations; the first polish chromatography unit operation precedes or follows the second polish chromatography unit operation; the virus inactivated elution pool can be neutralized using a neutralizing buffer system capable of minimizing volume expansion of a viral inactivated eluate pool while maintaining conductivity less than or equal to 10 ms/cm, wherein the buffer system includes a titrant that does not have buffer capacity in the target pH range and a buffering agent which buffers at a desired pH; the viral inactivation can be 30 minutes or more; the method can include subjecting the neutralized pool to a depth filtration operation; the method can include subjecting an elution of the one or more polish chromatography unit operations to one or more of: an ultrafiltration/diafiltration unit operation or a virus filtration unit operation; the affinity chromatography unit operation can be Protein A chromatography, Protein G chromatography, or Protein L chromatography; at least one of the one or more polish chromatography unit operations can be cation exchange chromatography, anion exchange chromatography, multi-modal chromatography, or hydrophobic interaction chromatography.

Any of the above forms can be a method for producing an isolated, purified, recombinant protein of interest. In accordance with third and fourth aspects, an isolated, purified, recombinant protein of interest of the above method is disclosed and a pharmaceutical composition including the isolated, purified, recombinant protein of interest of the above method is disclosed.

In accordance with a fifth aspect, a system for neutralizing a viral inactivated pool to a target pH with minimal volume expansion is disclosed that includes a titrant that does not have buffer capacity in a target pH range and a buffering agent which buffers at the target pH, where the conductivity of the neutralized viral inactivation elution pool is maintained at less than or equal to 10 ms/cm.

In some forms, the system can include one or more of the following aspects: the titrant can have a pKa greater than 7 and the buffering agent can have a pKa in the range of 4.5 to 6.0; the titrant can be acetate and the buffering agent can be Tris Base; the titrant can be in the range of greater than 0.1 M to less than 0.3 M sodium acetate; the buffering agent can be in the range of greater than 0.00005 M to less than 0.2 M Tris Base; the viral inactivation pool can be obtained by eluting an affinity chromatography column using a buffer comprising an acid having a pKa below 4 resulting in a virus inactivated elution pool with a pH of less than or equal to 3.6±0.1; the viral inactivation pool can have a pH less than or equal to 3.6±0.1, and can be obtained by eluting an affinity chromatography column using a buffer including a concentration of at least 50 mM to at least 150 mM, a pH range of 3.3 to 3.5, and an affinity chromatography pool volume of 2.1 CV to 7.7 CV and, in a further form, the viral inactivation pool can have a pH less than or equal to 3.6±0.1, and can be obtained by eluting an affinity chromatography column using a buffer including a concentration of 100 mM, a pH range of 3.3 to 3.5, and an affinity chromatography pool volume of 2.75 CV to 4.25 CV; the neutralizing buffer system can be used in a continuous flow process for purification of a protein of interest; or the neutralization can be achieved by combining a ratio of virus inactivation pool material with the neutralizing buffer system by flow into a static mixer.

DETAILED DESCRIPTION

Figure 1:
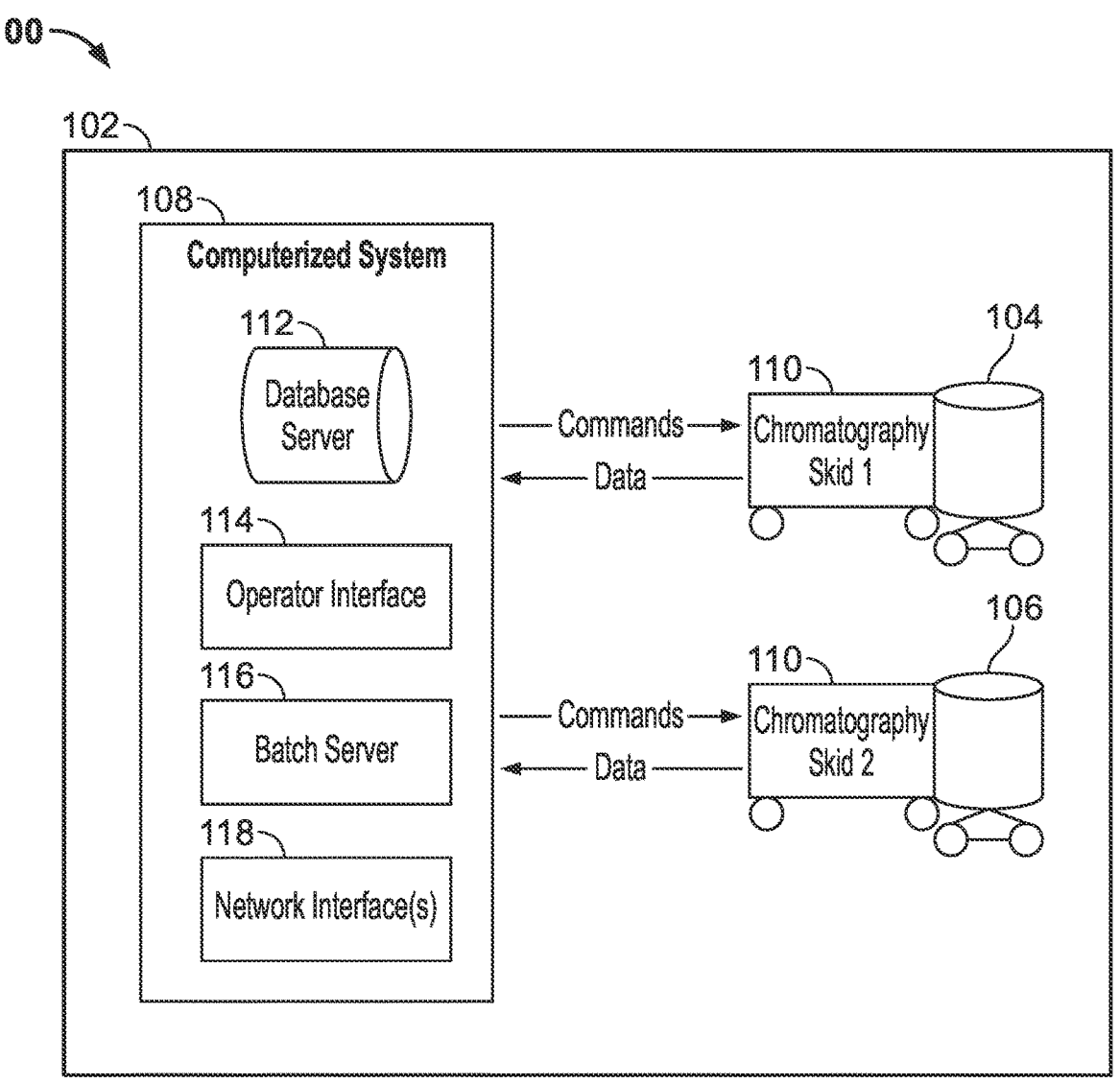
FIG. 1 is a diagrammatic view of a parallel process chromatography system in accordance with various embodiments of the disclosure.

The disclosure provided herein relates to process compression designed to improve purification for recombinant proteins, particularly those that have stability issues; minimize a processing footprint; make use of minimal equipment and facility size; and provide a simple and robust process, while achieving high throughput and productivity, and facilitating semi-continuous and/or continuous biomanufacturing, particularly at a small-scale. Described herein is a chromatography system that makes use of an unconnected parallel approach for continuous and semi-continuous manufacturing that utilizes two or more single column chromatography skids having no flow path between or connecting the skids that are operated in parallel with automation controls governing the processing of each skid independently.

This system and method furthers the pursuit of semi-continuous and continuous manufacturing processes, particularly at a smaller scale, by providing an automated parallel processing system for continuous processing (loading or eluting) on two or more independent, unconnected chromatography skids operating in parallel. The resulting system has advantages over the traditional large scale single column systems and multi-column fluidly connected systems by providing a purification system that is beneficial for recombinant proteins that have stability issues. The system also makes use of smaller columns, reduces use of chromatography material, provides more efficient column packing and use of chromatography material, has compatibility with and advantageously uses single use technologies, and is more efficient, timesaving, and flexible for downstream processing. The operation of the parallel skids is synchronized, with discrete events triggering communication between the skids. All of the above advantages reduce capital investments, such as by lowering equipment costs and/or processing time, without sacrificing the robustness of the manufacturing process.

The parallel chromatography processing system described herein makes more efficient use of time, for example by saving time during capture and/or elution cycles, as set forth in more detail below and in the figures, by allowing overlapping processing between the parallel skids. The parallel system is flexible, for example, enabling the performance of the final step on one skid while performing the penultimate step on a parallel skid, and/or compressing process time by increasing the speed during any cycle, particularly during the final cycle.

The parallel chromatography processing system supports chromatography operations that include the use of gradients for loading, washing, elution, and/or cleaning steps, as well as diluting buffer concentrates. This may require the use of two or more pumps per skid to perform efficiently perform these functions, something that would be difficult for multi-column serial systems to accommodate and execute.

The parallel chromatography processing system makes use of smaller columns, e.g., 2000 L or less, reduces the use of chromatography material, enables efficient column packing and use of chromatography resin by underloading the columns, which extends the resin half-life. The system is also able to make advantageous use of single use technology.

Moreover, the automation of the parallel chromatography process allows for a modular system comprising multiple single column skid units all controlled by a central automation system. The number of skids can be quickly and efficiently increased or decreased depending on the objectives of the manufacturing campaign. Due to the separate, parallel operation of the columns, an entire manufacturing run would not be lost or delayed in the event of a single skid failure, as happens during the operation of systems using skids comprising multiple columns with flow paths connected in series. This has been an issue with serial chromatography systems, such as PCC, where a single column failure can shut down an entire skid containing flow path connected columns that comprise one or more entire unit operations, delaying or even destroying an entire run. Such a failure impacts the drug substance supply, which can result in increased cost and delays delivery of drugs to patients in need.

Engineered proteins offer therapeutic advantages and improvements over traditional monoclonal antibody therapies and have become desirable next-generation biotherapeutics. As a result, these engineered proteins are being constructed in an increasing variety of formats to meet ever more challenging therapeutic indications. Engineered proteins, such as multispecific proteins, particularly bispecific antibodies, can be more sensitive to manufacturing processes than traditional monoclonal antibodies due to their engineered construction and, in some cases, higher titers. For such sensitive proteins, use of the parallel chromatography processing system described herein in downstream manufacturing operations provides a good compromise between flexibility, column efficiency and utilization, and desired product quality. The parallel chromatography system is beneficial in allowing processing at reduced titers without an increase in processing time. Purification of engineered proteins using current cycling strategies, such as serially connected chromatography systems like PCC, can result in poor product quality. The column overloading associated with serially connected systems can increase on-column aggregation, reduce the removal and/or cause the formation of impurities, such as high molecular weight (HMW) and/or low molecular weight (LMW) species that are commonly associated with engineered proteins and the high protein concentration on the purification columns and in the process pools.

One or more chromatography operations in a downstream manufacturing process may be performed using the parallel chromatography processing system described herein. The system is adaptable to any chromatography operation. As described herein and in the Figures, a downstream manufacturing platform may be comprised of one or more identical chromatography operations, one or more unique chromatography operations, and/or a combination of both.

The parallel chromatography processing system described herein is compatible with semi-continuous and continuous processing operations. The output from a parallel chromatography processing system may be selectively coupled to one or more downstream unit operations. This may be through a direct connection, surge tanks, holding tanks, bags, or other suitable containers adapted to accept a feed from at least one chromatography column skid or another unit operation. The combination of parallel chromatography processing systems with other unit operations to facilitate a continuous or semi-continuous process is also contemplated. Such combinations minimize processing time, resource use, facility footprint, and cost. For example, a parallel processing system employed in an affinity purification unit operation can be combined with a virus inactivation and neutralization unit operation designed to optimize processing and minimize buffer exchange and conditioning, particularly for smaller scale manufacturing operations. Described herein are affinity chromatography elution buffer formulations that achieve an eluate pool at a desired pH for virus inactivation. Also described are neutralizing buffer systems capable of robust bolus pH adjustment while minimizing volume expansion of the neutralized viral inactivation elution pool that achieves a desired conductivity.

General diagrams and example operation flowcharts for a parallel chromatography system 100 are shown in FIGS. 1-5. The system 100 includes a control circuit 102 configured to control the operation of first and second chromatography skids ("skid(s)") 104, 106. The control circuit 102 can include a central controller 108 remote from the skids 104, 106, as well as controllers 110 operating on each of the skids 104, 106. Communication signals between the controllers 108, 110 can be transmitted via wired and/or wireless connections, using any suitable network, including Wi-Fi, radio, near field communication, Bluetooth, etc. As such, each of the skids 104, 106, as well as the central controller 108, can include corresponding communication devices, including transmitters and receivers. In an alternative form, the control circuit 102 can include only controllers 110 operating on each of the skids 104, 106 that are in communication with one another. In one example, the central controller 108 can include a database server 112, an operator interface 114, a batch server 116, and network interface(s) 118. So configured, the control circuit 102 is operable to send commands to each of the skids 104, 106 to control the operation thereof and receive data and other signals from the skids 104, 106 in return. Although two skids 104, 106 are shown, it will be understood that the system 100 can be expanded to include any number of skids that may be desired for a particular process.

The term control circuit, as utilized herein, refers broadly to any combination of microcontrollers, computers, or processor-based devices with processor, memory, and programmable input/output peripherals, which are generally designed to govern the operation of other components and devices. It is further understood to include common accompanying accessory devices, including memory, transceivers for communication with other components and devices, etc. These architectural options are well known and understood in the art and require no further description here. The control circuit 102 may be configured (for example, by using a set of executable instructions/programming stored in a memory as will be well understood by those skilled in the art) to carry out one or more of the steps, actions, and/or functions described herein. In one example, open source language, such as Python, can be utilized to provide the programming to perform the operations and functions described herein.

As used herein, a "full cycle" of a chromatography process refers to the execution of the steps required for purification of a protein using the column 120 on one of the skids 104, 106. The typical steps in a full cycle for a chromatography column operated in bind and elute mode, for example, include equilibration of the column with a buffer that is compatible with the load buffer, the protein is then loaded onto the chromatography medium, and the chromatography medium is optionally washed with one or more wash buffers. The bound protein is then eluted from the column. Following elution, the column is cleaned which includes one or more steps of regeneration, stripping, and/or flushing. Each full cycle includes a "long step", the step in the full cycle that has the longest cycle time, and a series of "shorter steps" that are collectively shorter in cycle time or have a collective cycle time that is not longer in duration than the long step. Examples of a long step include the loading and/or the elution steps. Such steps can be longer in duration to maximize loading of protein on to a chromatography medium or to fully elute bound protein from the chromatography medium. The series of shorter processing steps collectively comprise a "production process cycle". Examples of shorter steps include the equilibration, one or more optional washes, and the cleaning steps, which may include one or more of a regeneration, strip, and/or flush step. The loading or elution steps are also included in the collection of shorter steps when they are not being operated as the long step. The flow rates of the short steps that make up the production process cycle can be chosen such that the production process cycle either ends in unison with the long step cycle, or at some point before the end of the long step cycle. In the latter case, a time gap may be added to the production process cycle to synchronize the production process cycle on one skid 104, 106 with the long step cycle on a parallel skid 104, 106.

Figure 2:
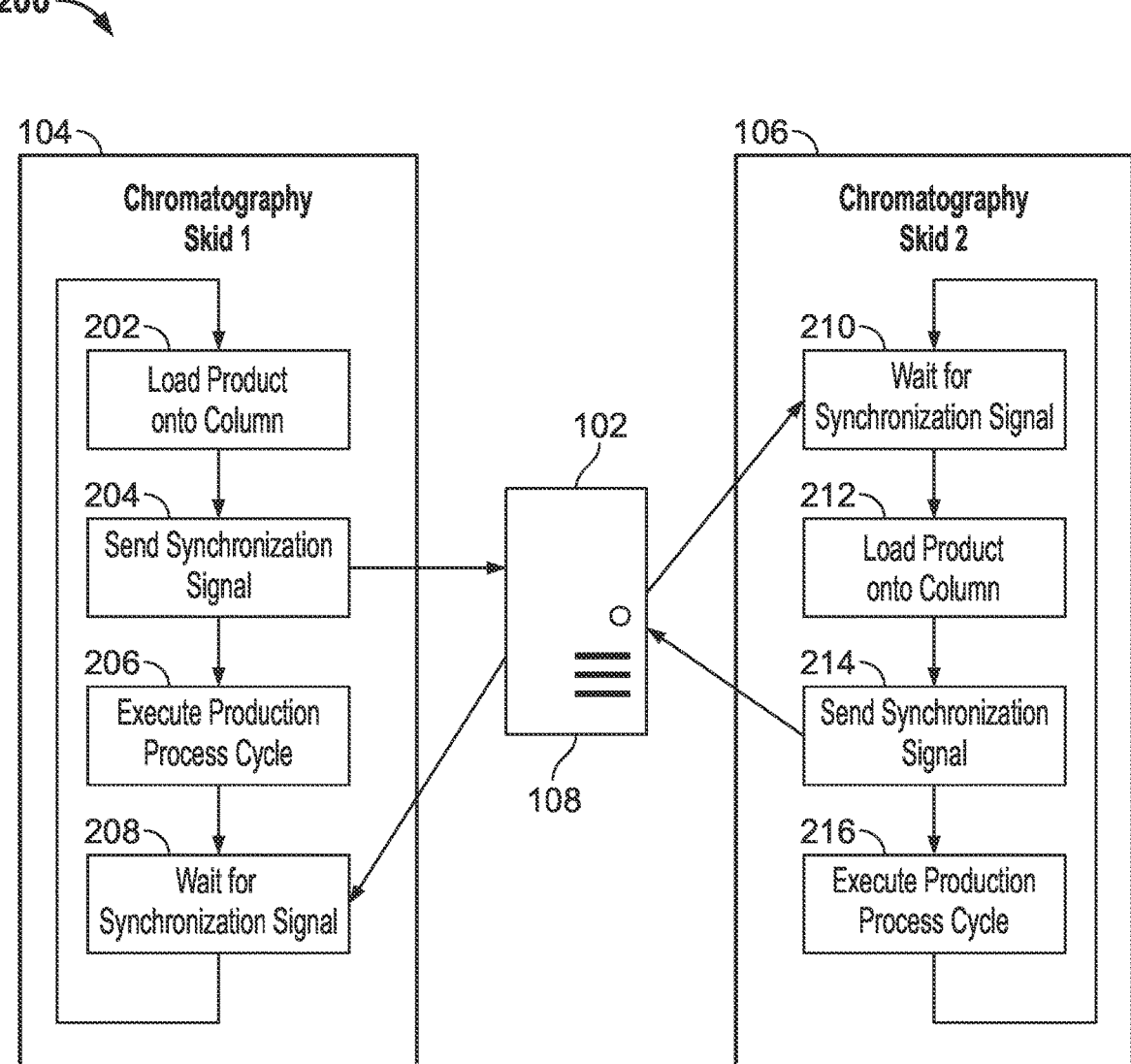
FIG. 2 is a flowchart for operating the parallel process chromatography system of FIG. 1 according to a first parallel cycling strategy using two affinity chromatography skids.

A first example operation process 200 for the parallel chromatography system 100 is shown in FIG. 2 where, such as for affinity chromatography, the longest step is loading the column. Although the process is described with reference to two skids 104, 106, it will be readily understood that the process can be expanded as desired.

In a first step 202, the control circuit 102 directs loading from a common feedstock onto the first skid 104 until a predetermined amount of the feedstock is loaded onto a column of the first skid 104. For example, a flow sensor, scale, timer, or other sensor can monitor the feedstock being dispensed to determine when a predetermined volume of feedstock suitable for the column of the first skid 104 has been dispensed. When the control circuit 102 determines that the predetermined amount of feedstock has been loaded onto the first skid 104, in a second step 204, the control circuit 102 generates/sends/receives a synchronization signal to begin loading common feedstock onto the second skid 106. For example, a controller 110 of the first skid 104 can generate and send the synchronization signal to the central controller 108. Alternatively, a controller 110 of the first skid 104 can generate and send the synchronization signal directly to the second skid 106. As used herein, a synchronization signal can be a discrete event triggers communicated between two or more units. The synchronization signal can be used to begin performance of a specified set of automated processing on any of the units. Thereafter, in a third step 206, the first skid 104 executes the production process cycle (e.g., one or more of: wash, elution, strip, regeneration, flush, equilibration) while a predetermined amount of the feedstock is loaded and bound onto a column of the second skid 106 and, in a fourth step 208, the first skid 104 waits for a synchronization signal to be generated from the second skid 106 that loading is complete, and loading can begin on the column of the first skid 104. In a fifth step 210, the second skid 106 waits for the synchronization signal according to the second step 204, while the first skid 104 is being loaded. When the synchronization signal for the first skid 104 is generated, in a sixth step 212, the control circuit 102 directs the loading of feedstock to the second skid 106 while the first skid 104 executes the production process cycle. Thereafter, when the control circuit 102 determines that the predetermined amount of feedstock has been loaded onto the column in the second skid 106, in a seventh step 214, the control circuit 102 generates/sends/receives a second synchronization signal and, in an eighth step 216, the second skid 106 executes the production process cycle while the first skid 104 is loaded. With this configuration, the loading of feedstock and the execution of the production process cycle can be continuously switched between two or more skids 104, 106 providing a continuous parallel processing method.

Figure 3:
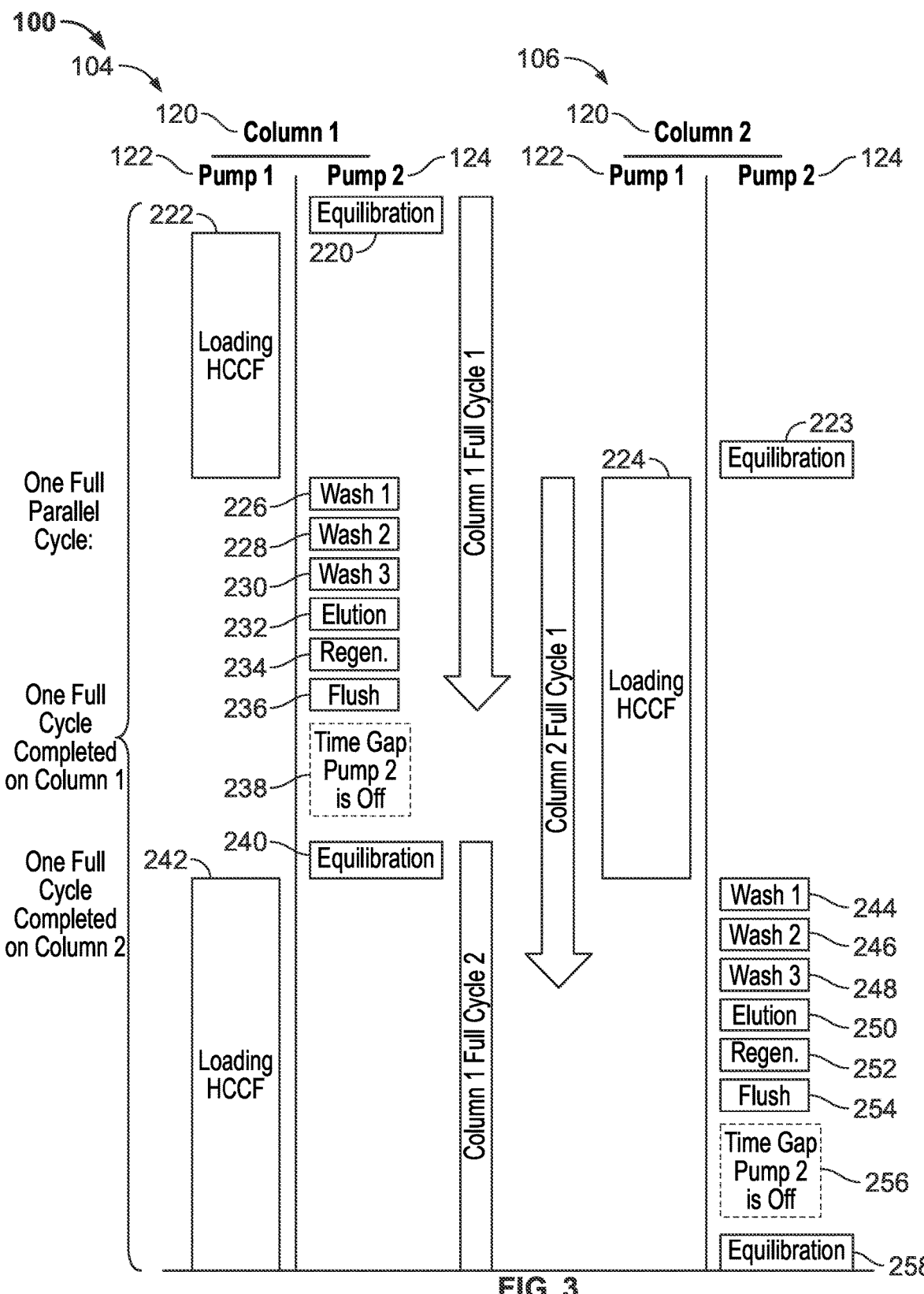
FIG. 3 is a flowchart for the parallel cycling strategy of FIG. 2 showing steps for columns of the two affinity chromatography skids utilizing at least first and second pumps.

FIG. 3 shows a flow chart for the cycling process for the parallel processing system 100 using two or more skids 104, 106 equipped with affinity chromatography columns 120, where the loading time for the chromatography column 120 is the long step in the unit operation. Each skid 104, 106 is shown as including two pumps 122, 124, one exclusive to loading and one for all other processing steps. It will be understood, however, that the first and second pumps 122, 124 can be a single pump, or can include one or a plurality of pumps for each pump 122, 124, if desired. Alternatively, the pumps 122, 124 can refer to one or more pumps that can be selectively coupled to each of the skids 104, 106, if desired.

As described in more detail below, while the long step of loading of feedstock, such as harvested host cell culture fluid (HCCF), is performed on the first skid 104 (Column 1), the smaller steps of the processing cycle (e.g., one or more of: wash, elution, strip, regeneration, and equilibration steps) is being performed on the second skid 106 (Column 2) that has just completed the loading cycle. In the processing cycle, the wash through equilibration steps are all preformed within the length of time of the loading cycle, or less. A time gap may be added to the processing cycle to synchronize the processing cycle timing to the loading cycle. For example, once the desired material has been eluted from the second skid 106 (Column 2) and the column 120 has been prepared for reloading, the second skid 106 (Column 2) is either just completing the processing cycle or is waiting for the synchronization signal to begin loading when the loading of the first skid (Column 1) is complete.

A "full cycle" refers to the complete process from feedstock load through flush/equilibration of the column 120 on one of the skids 104, 106. A "full parallel cycle" refers to a complete full cycle for each of at least two skids 104, 106 operating in parallel as shown in FIG. 3, for example. The steps of a full cycle can be performed with two or more pumps. Alternately, the steps in a full cycle can be performed using a single pump and timed valve switching to provide managed metered liquid solutions from two or three inlet channels.

FIG. 3 shows a full parallel cycle comprising a full cycle for column 1 and column 2, where the columns are affinity chromatography columns run in bind and elute mode. The loading step is the long step and the wash-equilibration steps are the short steps that make up the production process cycle. The process begins with the second pump 124 of the column 120 of the first skid 104 performing an equilibration step 220, after which the first pump 122 performs a loading step 222. After the loading step 222 for the column 120 of the first skid 104 has completed, and after an equilibration step 223 has been completed with the second pump 124, a loading step 224 for the column 120 of the second skid 106 is started with the first pump 122. This is achieved through the a synchronization signal as described above. While the column 120 of the second skid 106 is loading, the second pump 124 of the first skid 104 can sequentially perform optional first, second, and third washing steps 226, 228, 230, an elution step 232, a regeneration step 234, and a flushing step 236. This completes a full cycle for the column 120 of the first skid 104. If needed, to account for the longer loading times in the process 200, the second pump 124 of the first skid 104 can then shut off 238 for a predetermined time gap. The second pump 124 then performs an equilibration step 240 that generally, e.g., within between 0-10 minutes, ends the same time as the loading step 224 for the column 120 of the second skid 106 to start a subsequent cycle for the first skid 104. After the loading step 224 for the column 120 of the second skid 106 has completed, another loading step 242 for the column 120 of the first skid 104 is started. This is achieved through a synchronization signal as described above. While the column 120 of the first skid 104 is loading, the second pump 124 of the second skid 106 can sequentially perform optional first, second, and third washing steps 244, 246, 248, an elution step 250, a regeneration step 252, and a flushing step 254. This completes a full cycle for the column 120 of the second skid 106. As with the first skid 104, the second pump 124 of the second skid 106 can then shut off 256 for a predetermined time gap, if needed, and, subsequently perform an equilibration step 258 that generally ends the same time as the loading step 242 for the column 120 of the first skid 104.

In one embodiment, the flow rate is greater than or equal to 50 cm/hour. In one embodiment, the flow rate is at least 1000 cm/hour. In one embodiment the flow rate is 100 to 1000 cm/hour. In one embodiment the flow rate is 200 to 1000 cm/hour. In one embodiment the flow rate is 300 to 1000 cm/hour. In one embodiment the flow rate is 400 to 1000 cm/hour. In one embodiment the flow rate is 500 to 1000 cm/hour. In one embodiment the flow rate is 600 to 1000 cm/hour. In one embodiment the flow rate is 700 to 1000 cm/hour. In one embodiment the flow rate is 800 to 1000 cm/hour. In one embodiment the flow rate is 900 to 1000 cm/hour. In one embodiment the flow rate is 100 to 900 cm/hour. In one embodiment the flow rate is 200 to 900 cm/hour. In one embodiment the flow rate is 300 to 900 cm/hour. In one embodiment the flow rate is 400 to 900 cm/hour. In one embodiment the flow rate is 500 to 900 cm/hour. In one embodiment the flow rate is 600 to 900 cm/hour. In one embodiment the flow rate is 700 to 900 cm/hour. In one embodiment the flow rate is 800 to 900 cm/hour. In one embodiment the flow rate is 100 to 800 cm/hour. In one embodiment the flow rate is 200 to 800 cm/hour. In one embodiment the flow rate is 300 to 800 cm/hour. In one embodiment the flow rate is 400 to 800 cm/hour. In one embodiment the flow rate is 500 to 800 cm/hour. In one embodiment the flow rate is 600 to 800 cm/hour. In one embodiment the flow rate is 700 to 800 cm/hour. In one embodiment the flow rate is 100 to 700 cm/hour. In one embodiment the flow rate is 200 to 700 cm/hour. In one embodiment the flow rate is 300 to 700 cm/hour. In one embodiment the flow rate is 400 to 700 cm/hour. In one embodiment the flow rate is 500 to 700 cm/hour. In one embodiment the flow rate is 600 to 700 cm/hour. In one embodiment the flow rate is 100 to 600 cm/hour. In one embodiment the flow rate is 200 to 600 cm/hour. In one embodiment the flow rate is 300 to 600 cm/hour. In one embodiment the flow rate is 400 to 600 cm/hour. In one embodiment the flow rate is 500 to 600 cm/hour. In one embodiment the flow rate is 100 to 500 cm/hour. In one embodiment the flow rate is 200 to 500 cm/hour. In one embodiment the flow rate is 300 to 500 cm/hour. In one embodiment the flow rate is 400 to 500 cm/hour. In one embodiment the flow rate is 100 to 400 cm/hour. In one embodiment the flow rate is 200 to 400 cm/hour. In one embodiment the flow rate is 300 to 400 cm/hour. In one embodiment the flow rate is 100 to 300 cm/hour. In one embodiment the flow rate is 200 to 300 cm/hour. In one embodiment the flow rate is 100 to 100 cm/hour. In one embodiment the flow rate is 50 to 100 cm/hour. In one embodiment the flow rate is 50 to 200 cm/hour. In one embodiment the flow rate is 50 to 300 cm/hour. In one embodiment the flow rate is 50 to 400 cm/hour. In one embodiment the flow rate is 50 to 500 cm/hour. In one embodiment the flow rate is 50 to 600 cm/hour. In one embodiment the flow rate is 50 to 700 cm/hour. In one embodiment the flow rate is 50 to 800 cm/hour. In one embodiment the flow rate is 50 to 900 cm/hour. In one embodiment the flow rate is 50, 100, 150, 200, 250, 300, 350, 400, 450, 500, 550, 600, 650, 700, 750, 800, 850, 900, 950, or 1000 cm/hour.

The loading time will depend on the size of the column 120, the concentration of the protein in the feedstock, the flow rate, and/or the binding capacity of the chromatography medium being used. The loading time should be shorter than the allowable pool hold time (the protein's stability in the load pool). Loading time should meet the overall process requirements, e.g., target processing time. For example, processing times may be within 24 hours or within a single shift. Depending on the recombinant protein concentration in the feedstock, the loading time may be about 2 hours or less to about 24 hours.

In one embodiment the loading time is about 1 hour to about 24 hours. In one embodiment the loading time is about 12 hours to about 24 hours. In one embodiment the loading time is about 8 hours to about 12 hours. In one embodiment the loading time is about 5 hours to about 8 hours. In one embodiment the loading time is about 1 hour to about 5 hours. In one embodiment the loading time is about 2 hours to about 5 hours. In one embodiment the loading time is about 3 hours to about 5 hours. In one embodiment the loading time is about 4 hours to about 5 hours. In one embodiment the loading time is about 1 hour to about 4 hours. In one embodiment the loading time is about 2 hours to about 4 hours. In one embodiment the loading time is about 3 hours to about 4 hours. In one embodiment the loading time is about 1 hour to about 3 hours. In one embodiment the loading time is about 2 hours to about 3 hours. In one embodiment the loading time is about 1 to 2 hours. In one embodiment the loading time is about 1 hour, about 2 hours, about 3 hours, about 4 hours, about 5 hours, about 6 hours, about 7 hours, about 8 hours, about 9 hours, about 10 hours, about 11 hours, about 12 hours, about 16, hours, about 18 hours, or about 24 hours. Following loading, the affinity column 120 is processed with wash, elution, regeneration, flush and equilibration steps performed using the second pump 124. A valve system controlling the pumps 122, 124 is configured such to allow separate operation of the pumps 122, 124 as discussed below with reference to FIGS. 11 and 12.

To meet target processing times, the flow rate may be within 50 to 1000 cm/hour and the loading time may be within 1 to 24 hours.

A full parallel cycle may be 24 hours or a single shift. In one embodiment the full parallel cycle is about 5 hours to about 24 hours. In one embodiment the full parallel cycle is 12 to 24 hours. In one embodiment the full parallel cycle is 8 to 12 hours. In one embodiment the full parallel cycle is 5 to 8 hours. In one embodiment the full parallel cycle is 5 to 7 hours. In one embodiment the full parallel cycle is 5 to 6 hours. In one embodiment the full parallel cycle is 6 to 8 hours. In one embodiment the full parallel cycle is 6 to 7 hours. In one embodiment the full parallel cycle is 5 hours or less. In one embodiment the full parallel cycle is 1 to 5 hours. In one embodiment the full parallel cycle is 1 to 5 hours. In one embodiment, the full cycle is 2 to 5 hours. In one embodiment the full cycle is 3 to 5 cycles. In one embodiment the full cycle is 4 to 5 hours. In one embodiment the full cycle is 2 to 5 hours. In one embodiment the full cycle is 3 to 5 hours. In one embodiment the full cycle is 4 to 5 hours. In one embodiment the full cycle is 3 to 5 hours. Typically, the number of daily parallel cycles is from 1 to 5.

When purifying recombinant proteins, capture chromatography is typically performed following a cell culture harvest and is done to isolate and concentrate a protein of interest from a source medium such as the harvested cell culture fluid. Chromatography methods used during this capture phase are performed in bind and elute mode, under conditions where chromatography medium (resin or membrane) has an affinity or selectivity for the protein of interest which binds to the chromatography medium, while those components and/or impurities that have lesser affinity flow through or are not as strongly bound and can be removed or at least reduced by washing the chromatography material prior to elution.

Examples of capture chromatography materials include, but are not limited to, affinity chromatography (AC), size exclusion chromatography (SEC), ion exchange chromatography (IEX), hydrophobic interaction chromatography (HIC), multi-modal chromatography (MMC) and the like. Such materials are known in the art and are commercially available.

Affinity chromatography is commonly used in biomanufacturing processes as an initial capture step to isolate and concentrate recombinant proteins of interest having an Fc component. Examples of such affinity chromatography materials include those that make use of *Staphylococcus* proteins such as Protein A, Protein G, Protein A/G, and Protein L; substrate-binding capture mechanisms; antibody- or antibody fragment-binding capture mechanisms; aptamer-binding capture mechanisms; cofactor-binding capture mechanisms; and the like. Immobilized metal affinity chromatography can be used to capture proteins that have or have been engineered to have affinity for metal ions.

In one embodiment, two or more chromatography column skids 104, 106 each contain a single capture chromatography column 120. In one embodiment, the capture chromatography column 120 is an affinity chromatography column. In one embodiment, the affinity chromatography column 120 is a Protein A, Protein G, or Protein L chromatography column. In one embodiment, the affinity chromatography column 120 is a Protein A chromatography column.

Affinity chromatography material is available commercially from a number of vendors. For example, MABSE-LECT™ SURE Protein A, Protein A Sepharose FAST FLOW™ (Cytiva, Marborough, MA), PROSEP-A™ (Merck Millipore, U.K), TOYOPEARL™ 650M Protein A (TosoHass Co., Philadelphia, PA).

The capture chromatography operation is preferably performed using the continuous processing chromatography method as described herein. The method makes use of an automated parallel processing system that allows for continuous processing (loading to elution and any associated column processing and preparation steps) of the two or more chromatography columns cycling in parallel. This cycling strategy allows for continuous processing of the incoming feedstock, typically harvested host cell culture fluid (HCCP), and use of smaller chromatography columns. This process allows for a modular system that comprises at least two, and preferably multiple, single column skids 104, 106, all controlled by the central automation system 108 which offers the flexibility to increase or decrease the number of skids 104, 106 quickly and efficiently depending on the manufacturing objectives. Column switching saves time during the capture cycle and the process is relatively simple and robust and does not rely upon column overloading.

The chromatography column 120 may be equilibrated with a suitable buffer prior to being contacted with the feedstock containing the recombinant protein to be purified. Exemplary equilibration buffers include HEPES, Tris, phosphate, citrate, MES, BES, PIPES, Tricine, Bicine, TES, TAPSO, MOPS, and the like, at appropriate concentrations, conductivity, and/or pH for the material being purified.

Once the feedstock is loaded onto the column 120, the column is optionally washed with one or more wash solutions prior to the elution step. The wash step can be performed to bind any protein of interest that is still on the column, but not yet bound to the chromatography material, flush out load material from the interstitial spaces, remove impurities that have bound to and/or are within the chromatography medium, and/or to prepare the column 120 for elution. Multiple wash solutions may be used depending on the purpose and number of the wash steps. Wash buffers can include use of equilibration buffers and loading buffers. Buffer formulations include tris buffer or phosphate; salts, such as sodium acetate, sodium citrate, or sodium chloride; divalent cations such as calcium, magnesium, or nickel; detergents polymers, amino acids, sugar alcohols, and/or chaotropic agents, among others. Where multiple wash buffers are used, the composition and/or concentration of wash buffer formulations may be the same or differ as needed. Washes are performed at appropriate pH, typically at neutral pH, but can be performed at higher or lower pH as needed.

The bound recombinant protein is eluted from the column 120 by altering the buffer conditions. Elution may be isocratic, gradient, or other suitable method or combination of methods. Elution is typically performed under low pH conditions, elution buffers include acids such as acidic, citric, formic, phosphoric acid, alone or in combination with buffers, amino acids, salts, and the like.

Suitable methods and buffers are known for cleaning and regenerating capture chromatography medium.

The capture chromatography may be run continuously during the cell culture steady state. A small surge vessel (surge bag) may be used to buffer small variations in flow and provide an air break between the bioreactor and a harvest unit operation. The capture chromatography may be run continuously during the harvest unit operation or run from harvest hold vessels.

Following affinity purification, the recombinant protein is typically subjected to one or more additional purification steps for further resolution of the protein of interest from remaining contaminants and impurities. The term "polish" or "polishing" is used herein to refer to one or more chromatographic steps performed to remove remaining contaminants and impurities such as DNA, host cell proteins; product-related impurities, aggregates, viruses and the like, as well as facilitating changes in pH, concentration, and buffer formulations, that bring the recombinant protein of interest closer to a final desired purity.

A polish chromatography unit operation makes use of chromatography media, such as resins and/or membranes, containing agents that can be used in either a bind and elute mode (where the protein of interest is bound to the chromatography medium and eluted after the contaminants and impurities have flowed through or been washed off the chromatography medium), frontal or overloaded mode (where a solution containing the protein of interest is loaded onto a column until adsorption sites on are occupied and the species with the least affinity for the stationary phase (the protein of interest) starts to elute), a flow-through mode (where the protein of interest flows through the chromatographic material without binding and the contaminants and impurities are bound to the chromatography medium), or by any other mode or a combination of modes. Examples of chromatography modalities used for the polish step include, but are not limited to, ion exchange chromatography (IEX), such as anion exchange chromatography (AEX) and cation exchange chromatography (CEX); hydrophobic interaction chromatography (HIC); mixed modal or multi-modal chromatography (MMC), hydroxyapatite chromatography (HA); reverse phase chromatography, affinity chromatography (AC), and gel filtration.

Each of the polish chromatography unit operations may be run in the same or different configurations and/or different modes. Each chromatography unit may be run as a single unconnected unit, multiple connected units, and/or combined units. Single chromatography columns may be run in a staggered cycling system, counter current loading (periodic counter current chromatography), or as a multicolumn counter current solvent gradient purification process (MCSGP), for example.

Multiple chromatography unit operations, typically one, two, or three, each performing the same or different functions, are combined depending on the requirements of the manufacturing process. Ion exchange chromatography, based on electrostatic interactions between charged surfaces, separates proteins of interest from impurities based on differential absorption and desorption. Cation exchange chromatography refers to chromatography performed on a solid phase medium that is negatively charged and has free cations for exchange with cations in an aqueous solution passed over or through the solid phase. The charge may be provided by attaching one or more charged ligands to the solid phase, e.g. by covalent linking. Alternatively, or in addition, the charge may be an inherent property of the solid phase (e.g. as is the case for silica, which has an overall negative charge). Cation exchange chromatography is typically run in bind and elute mode, the high isoelectric point (pI) of many proteins of interest enable binding to the chromatography material. Cation exchange chromatography may also be run in flow through mode. CEX chromatography is typically used to remove high molecular weight (HMW) contaminants, process related impurity, and/or viral clearance. Commercially available cation exchange mediums are available and include but are not limited to sulphopropyl (SP) immobilized on agarose (e.g. SP-SEPHAROSE FAST FLOW™, SP-SEPHAROSE FAST FLOW XL™ or SP-SEPHAROSE HIGH PERFORMANCE™, CAPTO S™, CAPTO SP ImpRes™, CAPTO S ImpAct™ (Cytiva), FRACTOGEL-SO3™, FRACTOGEL-SE HICAP™, and FRACTOPREP™ (EMD Merck, Darmstadt, Germany), TOYOPEARL® XS, TOYOPEARL® HS (Tosh Bioscience, King of Prussia, PA), UNOsphere™ (BioRad, Hercules, CA), S Ceramic Hyper D™F (Pall, Port Washington, NY), POROS™ (ThermoFisher, Waltham, MA).

Anion exchange chromatography refers to chromatography performed on a solid phase medium that is positively charged and has free anions for exchange with anions in an aqueous solution passed over or through the solid phase. Anion exchange chromatography is typically run in flow through mode. Due to the high pI of many proteins of interest they do not to bind to the AEX chromatography material. AEX chromatography is used, for example, for viral clearance and impurity removal. Commercially available anion exchange mediums are available and include, but are not limited to, sulphopropyl (SP) immobilized on agarose (e.g. Source 15 Q, Capto™ Q, Q-SEPHAROSE FAST FLOW™ (Cytiva), FRACTOGEL EDM TMAE™, FRAC-TOGEL EDM DEAE™ (EMD Merck), TOYOPEARL Super Q® (Tosh Bioscience), POROS HQ™, POROS XQ™, (ThermoFisher).

Mixed-mode or multi-mode chromatography (MMC) refers to chromatography performed on a solid phase medium that makes use of a combination of interaction mechanisms, such as ion exchange (CEX or AEX) and hydrophobic interaction, and others. Commercially available multi-modal chromatography media are available, an example is Capto™ Adhere Anion Exchange Multi Mode.

Hydrophobic interaction chromatography refers to chromatography performed on a solid phase medium that makes use of the interaction between hydrophobic ligands and hydrophobic residues on the surface of a protein of interest. Commercially available hydrophobic interaction chromatography media includes but are not limited to Phenyl Sepharose™, Tosoh hexyl, and Capto™ phenyl.

Hydroxyapatite chromatography refers to chromatography performed on a solid phase medium that makes use of positively charged calcium and negatively charged phosphate and depending on the pI of the protein and the pH of the buffer, can act as a cation or anion.

An eluate stream or pool containing a recombinant protein of interest may be loaded onto the polish chromatography column, particularly in such a manner that the protein of interest is bound to the chromatography medium. The eluate stream may be loaded onto the polish chromatography column in such a manner that the protein of interest is not bound to the chromatography medium. The eluate stream or pool may have originated from a previous unit operation, such as cell culture harvest fluid, affinity chromatography, virus inactivation, virus filtration, depth filtration, and/or another polish chromatography operation. Additional buffer may be added to the eluate or pool such that the final load is at a desired concentration and/or formulation.

The loading material for a polish unit operation may be a pool or eluate from a virus inactivation unit operation, in particular from a low pH virus inactivation unit operation, for example a neutralized virus inactivated pool or eluate.

In one aspect, two or more polish chromatography columns may be connected in series and run in flow through mode as one polish chromatography unit. The combined columns can be operated as a complete polish chromatography unit operation or used in combination with one or more additional polish chromatography units run in bind and elute mode, frontal mode, and/or flow through mode.

As described herein, one or more polish chromatography unit operations may be performed using the continuous process chromatography method described herein that makes use of the parallel process system 100.

Figure 4:
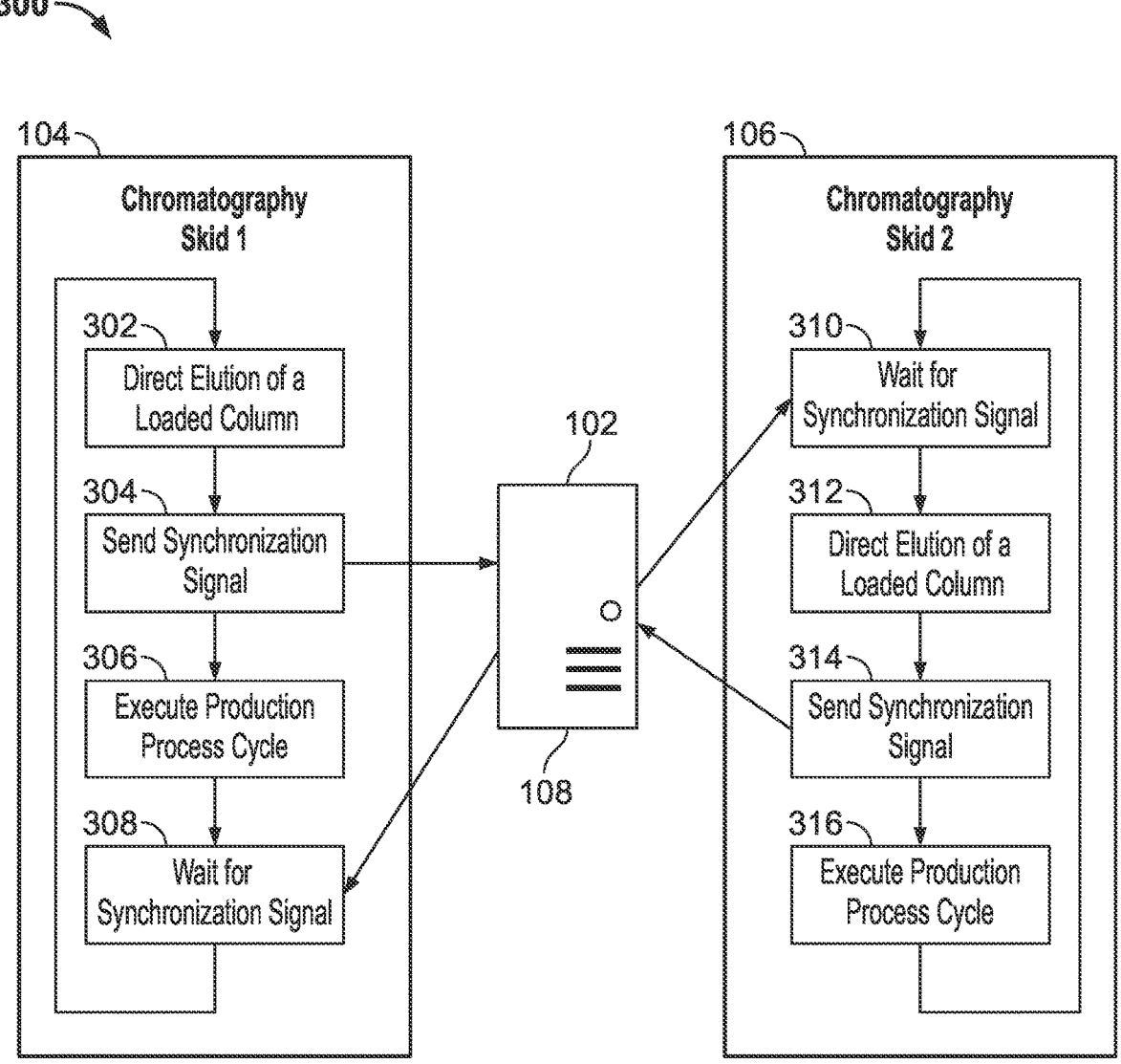
FIG. 4 is a flowchart for operating the parallel process chromatography system of FIG. 1 according to a second parallel cycling strategy using two cation exchange chromatography skids.

Two or more similar chromatography column skids 104, 106 may be run in parallel and controlled by the continuous parallel chromatography system 100 as described herein. In one embodiment two or more similar chromatography column skids 104, 106 each contain the same type of polish chromatography column 120. FIG. 4 shows the cycling process for an exemplary system using two or more skids 104, 106 each equipped with a cation exchange chromatography column operated in bind and elute mode, where the elution time for the chromatography column is the long step in the unit operation cycle.

An example operation process 300 for the parallel chromatography system 100 is shown in FIG. 4 where, such as for polish chromatography, the longest step is eluting the column. Although the process is described with reference to two skids 104, 106, it will be readily understood that the process can be expanded as desired.

In a first step 302, the control circuit 102 directs the elution of a loaded column of the first skid 104 until a predetermined amount of the purified protein is eluted from the column. For example, as described below, a flow sensor, scale, timer, or other sensor can monitor the eluate to determine when a desired amount of a protein of interest has been eluted. When the control circuit 102 determines that the predetermined protein titer has been eluted from the first skid 104, in a second step 304, the control circuit 102 generates/sends/receives a synchronization signal to begin eluting protein from the column of the second skid 106. For example, a controller 110 of the first skid 104 can generate and send the synchronization signal to the central controller 108. Alternatively, a controller 110 of the first skid 104 can generate and send the synchronization signal directly to the second skid 106. Thereafter, in a third step 306, the first skid 104 executes the production process cycle (e.g., one or more of: strip, regenerate, flush, equilibrate, load, and wash steps) while a predetermined protein titer is eluted from the column of the second skid 106 and, in a fourth step 308, the first skid 104 waits for a synchronization signal to be generated from the second skid 106 that elution is complete, and elution can begin on the column of the first skid 104. In a fifth step 310, the second skid 106 waits for the synchronization signal to be generated according to the second step 304, while the first skid 104 is being eluted. When the synchronization signal for the first skid 104 is generated, in a sixth step 312, the control circuit 102 directs the elution of protein from the column of the second skid 106 while the first skid 104 executes the production process cycle in the third step 306. Thereafter, when the control circuit 102 determines that the predetermined protein titer has been eluted from the column of the second skid 106, in a seventh step 314, the control circuit 102 generates/sends/receives a second synchronization signal and, in an eighth step 316, the second skid 106 executes the production process cycle while the first skid 104 is eluted. With this configuration, the elution of protein and the execution of the production process cycle can be continuously switched between two or more skids 104, 106 providing a continuous parallel processing method.

Figure 5:
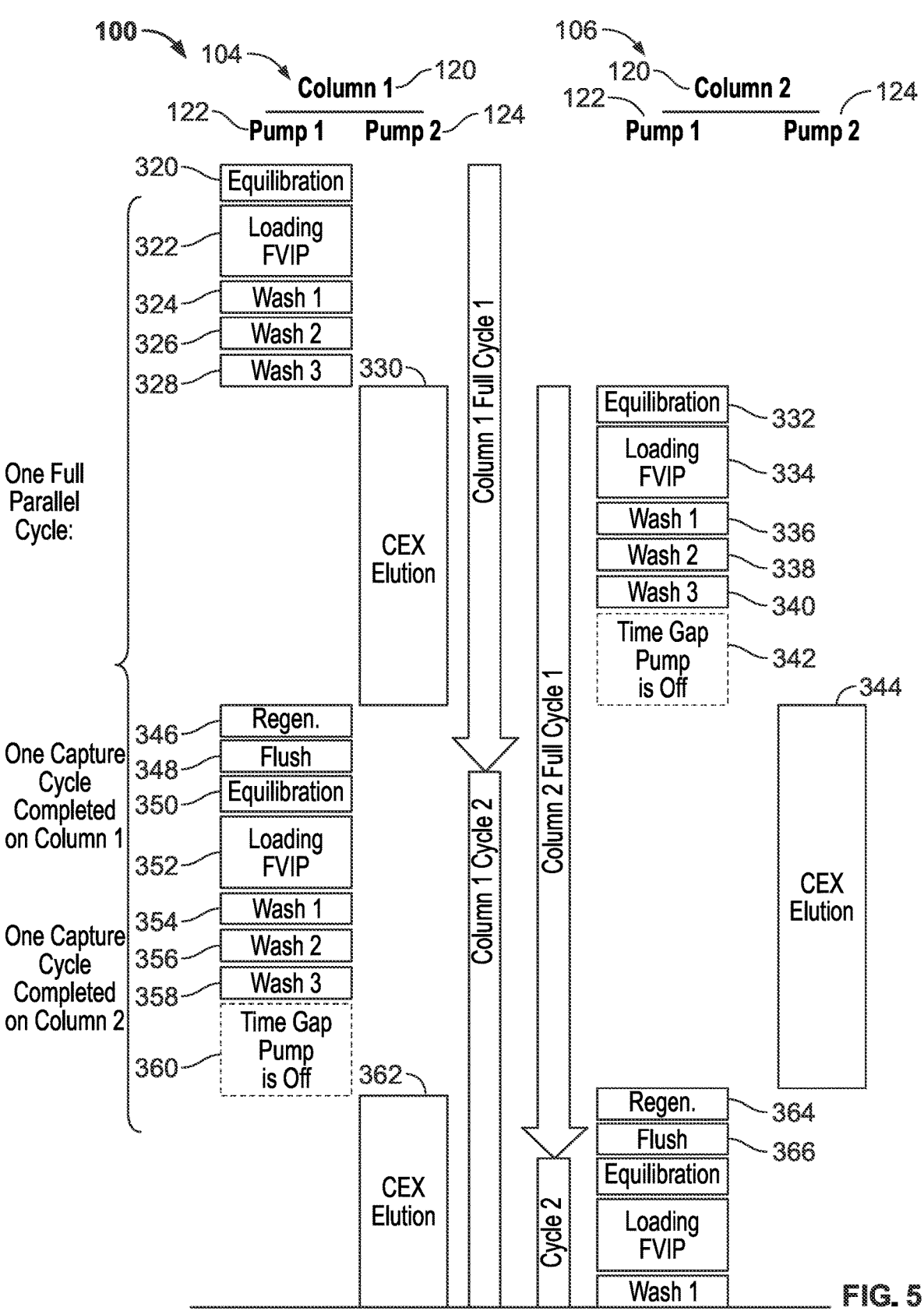
FIG. 5 is a flowchart for the parallel cycling strategy of FIG. 4 showing steps for columns of the two cation exchange chromatography skids utilizing at least first and second pumps.

A flow chart showing the processing steps for each of the skids 104, 106 according to the process 300 of FIG. 4 is shown in FIG. 5. Each skid 104, 106 includes a chromatography column 120 with associated first and second pumps 122, 124, where one pump 124 is exclusive to elution and one pump 122 is utilized for all other processing steps. It will be understood, however, that the first and second pumps 122, 124 can be a single pump, or can include one or a plurality of pumps for each pump 122, 124, if desired. Alternatively, the pumps 122, 124 can refer to one or more pumps that can be selectively coupled to each of the skids 104, 106, if desired.

In this form, the system 100 operates in bind and elute mode with a gradient elution. The process begins with the first pump 122 of the first skid 104 performing an equilibration step 320, a loading step 322, and one or more optional washing steps 324, 326, 328. After the washing step

328 for the column 120 of the first skid 104 has completed, the second pump 124 of the first skid 104 begins an elution step 330 for the column 120. While the column 120 of the first skid 104 is eluting, the first pump 122 of the second skid 106 sequentially performs an equilibration step 332, a loading step 334, and first, second, and third optional washing steps 336, 338, 340. Thereafter, if needed to account for the longer elution times in the process 300, the first pump 122 of the second skid 106 can then shut off 342 for a predetermined time gap. After the elution step 330 for the first skid 104 has completed, the second pump 124 of the second skid 106 begins an elution step 344 for the column 120. This is achieved through a synchronization signal as described above. While the column 120 of the second skid 106 is eluting, the first pump 122 of the first skid 104 performs a regeneration step 346 and a flushing step 348 to complete a full cycle for the column 120. The first pump 122 then begins a new cycle with the first pump 122 of the first skid 104 performing an equilibration step 350, a loading step 352, and first, second, and third optional washing steps 354, 356, 358, followed by the first pump 122 shutting off 360 for a predetermined time gap, if needed, to account for the longer elution time for the column 120 of the second skid 106. After the elution step 344 for the second skid 106 has completed, the second pump 124 of the first skid 104 begins another elution step 362 for the column 120. This is achieved through a synchronization signal as described above. While the column 120 of the first skid 104 is eluting, the first pump 122 of the second skid 104 performs a regeneration step 364 and a flushing step 366 to complete a full cycle for the column 120.

In the processing cycle, the regeneration step through the wash steps are all preformed within the length of time of the elution cycle, or less. As such, a time gap may be added to the processing cycle to synchronize the processing cycle timing to the elution cycle. The cycles can be defined as best fits any parameter in the process infrastructure, for example, the size of the column 120, the concentration of the bound protein, the binding capacity of the chromatography medium being used, and/or the desired titer in the elution pool.

The elution time will depend on the chromatography mode, the concentration of the bound protein, the slope or rate of change of any gradient, and/or the binding capacity of the chromatography medium being used. Elution time should meet the overall process requirements, e.g., target processing time. For example, such target processing times may be within 24 hours or within 1 shift. Typically, such elution time is about 2 hours or less, depending on the amount of protein bound to the chromatography medium. In one embodiment, each full parallel cycle is typically completed in 5 to 8 hours.

In one embodiment the elution time is about 1 hour to about 24 hours. In one embodiment the elution time is about 12 hours to about 24 hours. In one embodiment the elution time is about 8 hours to about 12 hours. In one embodiment the loading time is about 5 hours to about 8 hours. In one embodiment the elution time is about 1 hour to about 5 hours. In one embodiment the elution time is about 2 hours to about 5 hours. In one embodiment the elution time is about 3 hours to about 5 hours. In one embodiment the elution time is about 4 hours to about 5 hours. In one embodiment the elution time is about 1 hour to about 4 hours. In one embodiment the elution time is about 2 hours to about 4 hours. In one embodiment the elution time is about 3 hours to about 4 hours. In one embodiment the elution time is about 1 hour to about 3 hours. In one embodiment the elution time is about 2 hours to about 3 hours. In one embodiment the elution time is about 1 to 2 hours. In one embodiment the elution time is about 1 hour, about 2 hours, about 3 hours, about 4 hours, about 5 hours, about 6 hours, about 7 hours, about 8 hours, about 9 hours, about 10 hours, about 11 hours, about 12 hours, about 16 hours, about 18 hours, or about 24 hours. Following elution, the polish chromatography column 120 is processed with regeneration, flush, equilibration, load, and wash steps performed using the first pump 122.

The flow rate should meet process requirements e.g., target processing time. For example, such target flow rates may be within 50 to 1000 cm/hour. In one embodiment, the flow rate is greater than or equal to 50 cm/hour. In one embodiment, the flow rate is at least 1000 cm/hour. In one embodiment the flow rate is 100 to 1000 cm/hour. In one embodiment the flow rate is 200 to 1000 cm/hour. In one embodiment the flow rate is 300 to 1000 cm/hour. In one embodiment the flow rate is 400 to 1000 cm/hour. In one embodiment the flow rate is 500 to 1000 cm/hour. In one embodiment the flow rate is 600 to 1000 cm/hour. In one embodiment the flow rate is 700 to 1000 cm/hour. In one embodiment the flow rate is 800 to 1000 cm/hour. In one embodiment the flow rate is 900 to 1000 cm/hour. In one embodiment the flow rate is 100 to 900 cm/hour. In one embodiment the flow rate is 200 to 900 cm/hour. In one embodiment the flow rate is 300 to 900 cm/hour. In one embodiment the flow rate is 400 to 900 cm/hour. In one embodiment the flow rate is 500 to 900 cm/hour. In one embodiment the flow rate is 600 to 900 cm/hour. In one embodiment the flow rate is 700 to 900 cm/hour. In one embodiment the flow rate is 800 to 900 cm/hour. In one embodiment the flow rate is 100 to 800 cm/hour. In one embodiment the flow rate is 200 to 800 cm/hour. In one embodiment the flow rate is 300 to 800 cm/hour. In one embodiment the flow rate is 400 to 800 cm/hour. In one embodiment the flow rate is 500 to 800 cm/hour. In one embodiment the flow rate is 600 to 800 cm/hour. In one embodiment the flow rate is 700 to 800 cm/hour. In one embodiment the flow rate is 100 to 700 cm/hour. In one embodiment the flow rate is 200 to 700 cm/hour. In one embodiment the flow rate is 300 to 700 cm/hour. In one embodiment the flow rate is 400 to 700 cm/hour. In one embodiment the flow rate is 500 to 700 cm/hour. In one embodiment the flow rate is 600 to 700 cm/hour. In one embodiment the flow rate is 100 to 600 cm/hour. In one embodiment the flow rate is 200 to 600 cm/hour. In one embodiment the flow rate is 300 to 600 cm/hour. In one embodiment the flow rate is 400 to 600 cm/hour. In one embodiment the flow rate is 500 to 600 cm/hour. In one embodiment the flow rate is 100 to 500 cm/hour. In one embodiment the flow rate is 200 to 500 cm/hour. In one embodiment the flow rate is 300 to 500 cm/hour. In one embodiment the flow rate is 400 to 500 cm/hour. In one embodiment the flow rate is 100 to 400 cm/hour. In one embodiment the flow rate is 200 to 400 cm/hour. In one embodiment the flow rate is 300 to 400 cm/hour. In one embodiment the flow rate is 100 to 300 cm/hour. In one embodiment the flow rate is 200 to 300 cm/hour. In one embodiment the flow rate is 100 to 100 cm/hour. In one embodiment the flow rate is 50 to 100 cm/hour. In one embodiment the flow rate is 50 to 200 cm/hour. In one embodiment the flow rate is 50 to 300 cm/hour. In one embodiment the flow rate is 50 to 400 cm/hour. In one embodiment the flow rate is 50 to 500 cm/hour. In one embodiment the flow rate is 50 to 600 cm/hour. In one embodiment the flow rate is 50 to 700 cm/hour. In one embodiment the flow rate is 50 to 800 cm/hour. In one embodiment the flow rate is 50 to 900 cm/hour. In one embodiment the flow rate is 50, 100, 150, 200, 250, 300, 350, 400, 450, 500, 550, 600, 650, 700, 750, 800, 850, 900, 950, or 1000 cm/hour.

To meet target processing times, the flow rate may be within 50 to 1000 cm/hour and the elution time may be within 1 to 24 hours.

A full parallel cycle may be 24 hours or a single shift. In one embodiment the full parallel cycle is about 5 hours to about 24 hours. In one embodiment the full parallel cycle is 12 to 24 hours. In one embodiment the full parallel cycle is 8 to 12 hours. In one embodiment the full parallel cycle is 5 to 8 hours. In one embodiment the full parallel cycle is 5 to 7 hours. In one embodiment the full parallel cycle is 5 to 6 hours. In one embodiment the full parallel cycle is 6 to 8 hours. In one embodiment the full parallel cycle is 6 to 7 hours. In one embodiment the full parallel cycle is 5 hours or less. In one embodiment the full parallel cycle is 1 to 5 hours. In one embodiment the full parallel cycle is 1 to 5 hours. In one embodiment, the full cycle is 2 to 5 hours. In one embodiment the full cycle is 3 to 5 cycles. In one embodiment the full cycle is 4 to 5 hours. In one embodiment the full cycle is 2 to 5 hours. In one embodiment the full cycle is 3 to 5 hours. In one embodiment the full cycle is 4 to 5 hours. In one embodiment the full cycle is 3 to 5 hours. Typically, the number of daily parallel cycles is from 1 to 5.

The bound recombinant protein may be eluted from the column 120 by altering the buffer conditions. Elution may be isocratic, gradient, or other suitable method or combination of methods.

The rate or slope of a gradient may be measured as mM of salt/column volume (CV) of elution buffer. For example, for a sodium chloride gradient from 0 mM to 1000 mM, a typical range of slopes used for elution would be 5 mM salt/CV to 50 mM/CV. In one embodiment, the slope is from 5 mM/CV to 20 mM/CV. The elution duration is typically greater than 0 CV to 1000V. In one embodiment the elution duration is greater than 0 CV to 20 CV.

The chromatography column 120 may be equilibrated with a suitable buffer prior to being contacted with the feedstock containing the recombinant protein to be purified. Exemplary equilibration buffers include HEPES, Tris, phosphate, citrate, MES, BES, PIPES, Tricine, Bicine, TES, TAPSO, MOPS, and the like, at appropriate concentrations, conductivity and/or pH for the material being purified.

Once the feedstock is loaded onto the column 120, the column is optionally washed with one or more wash solutions prior to the elution step. The wash step can be performed to bind any protein of interest that is still on the column but not yet bound to the chromatography material, flush out load material from the interstitial spaces, remove impurities that have bound to and/or are within the chromatography medium, and/or to prepare the column 120 for elution. Multiple wash solutions may be used depending on the purpose and number of the wash steps. Wash buffers can include use of equilibration buffers and loading buffers. Typical buffer formulations include tris buffer or phosphate; salts, such as sodium acetate, sodium citrate, or sodium chloride; divalent cations such as calcium, magnesium, or nickel, detergents polymers, amino acids, sugar alcohols, and/or chaotropic agents, among others. Where multiple wash buffers are used, the composition and/or concentration of wash buffer formulations may differ as needed. Washes are performed at appropriate pH, typically at neutral pH, but can be performed at higher or lower pH as needed.

The bound recombinant protein is eluted from the column 120 by altering the buffer conditions. Elution may be isocratic, gradient, or other suitable method or combination of methods. Elution is performed under pH, salt and/or buffer conditions suitable for the protein being eluted. Typical buffer formulations include tris buffer or phosphate; salts, such as sodium acetate, sodium citrate, or sodium chloride; divalent cations such as calcium, magnesium, or nickel, detergents polymers, amino acids, sugar alcohols, and/or chaotropic agents, among others.

Suitable methods and buffers are known for cleaning and regenerating polish chromatography medium.

Multiple chromatography unit operations, typically one, two, or three, each performing a different function, are combined depending on the requirements of the manufacturing process. Ion exchange chromatography, based on electrostatic interactions between charged surfaces, separates proteins of interest from impurities based on differential absorption and desorption. Cation exchange chromatography refers to chromatography performed on a solid phase medium that is negatively charged and has free cations for exchange with cations in an aqueous solution passed over or through the solid phase. The charge may be provided by attaching one or more charged ligands to the solid phase, e.g. by covalent linking. Alternatively, or in addition, the charge may be an inherent property of the solid phase (e.g. as is the case for silica, which has an overall negative charge). Cation exchange chromatography is typically run in bind and elute mode, the high pI of many proteins of interest enable binding to the chromatography material. Cation exchange chromatography may also be run in flow through mode. CEX chromatography is typically used to remove high molecular weight (HMW) contaminants, process related impurity, and/or viral clearance. Commercially available cation exchange mediums are available and include but are not limited to sulphopropyl (SP) immobilized on agarose (e.g. SP-SEPHAROSE FAST FLOW™, SP-SEPHAROSE FAST FLOW XL™ or SP-SEPHAROSE HIGH PERFORMANCE™, CAPTO S™, CAPTO SP ImpRes™, CAPTO S ImpAct™ (Cytiva), FRACTOGEL-SO3™, FRACTOGEL-SE HICAP™, and FRACTOPREP™ (EMD Merck, Darmstadt, Germany), TOYOPEARL® XS, TOYOPEARL® HS (Tosh Bioscience, King of Prussia, PA), UNOsphere™ (Bio-Rad, Hercules, CA), S Ceramic Hyper D™F (Pall, Port Washington, NY), POROS™ (ThermoFisher, Waltham, MA).

Anion exchange chromatography refers to chromatography performed on a solid phase medium that is positively charged and has free anions for exchange with anions in an aqueous solution passed over or through the solid phase. Anion exchange chromatography is typically run in flow through mode. Due to the high pI of many proteins of interest they do not to bind to the AEX chromatography material. AEX chromatography is used, for example, for viral clearance and impurity removal. Commercially available anion exchange mediums are available and include, but are not limited to, sulphopropyl (SP) immobilized on agarose (e.g. Source 15 Q, Capto™ Q, Q-SEPHAROSE FAST FLOW™ (Cytiva), FRACTOGEL EDM TMAE™, FRACTOGEL EDM DEAE™ (EMD Merck), TOYOPEARL Super Q® (Tosh Bioscience), POROS HQ™, POROS XQ™, (ThermoFisher).

Mixed-mode or multi-mode chromatography (MMC) refers to chromatography performed on a solid phase medium that makes use of a combination of interaction mechanisms, such as ion exchange (CEX or AEX) and hydrophobic interaction, and others. Commercially available multi-modal chromatography media are available and include but are not limited to Capto™ Adhere Anion Exchange Multi Mode, PPA Hypercel, and HEA Hypercel.

Hydrophobic interaction chromatography refers to chromatography performed on a solid phase medium that makes use of the interaction between hydrophobic ligands and hydrophobic residues on the surface of a protein of interest. Commercially available hydrophobic interaction chromatography media includes but are not limited to Phenyl Sepharose™, Tosoh hexyl, and Capto™ phenyl.

Hydroxyapatite chromatography refers to chromatography performed on a solid phase medium that makes use of positively charged calcium and negatively charged phosphate and depending on the pI of the protein and the pH of the buffer, can act as a cation or anion.

In one embodiment, two or more polish chromatography columns are connected in series and run in flow through mode as one polish chromatography unit. The combined columns can be operated as a complete polish chromatography unit operation or used in combination with one or more additional polish chromatography units run in bind and elute mode and/or flow through mode.

An eluate stream or pool containing a protein of interest may be loaded onto the polish chromatography column, particularly in such a manner that the protein of interest is bound to the chromatography medium. The eluate stream may be loaded onto the polish chromatography column in such a manner that the protein of interest is not bound to the chromatography medium. The eluate stream or pool may have originated from a previous unit operation, such as cell culture harvest fluid, affinity chromatography, virus inactivation, virus filtration, depth filtration, and/or another polish chromatography operation. Additional buffer may be added to the eluate or pool such that the final load of the protein is at a desired concentration and/or formulation.

The loading material for a polish unit operation may be a pool or eluate from a virus inactivation unit operation, in particular from a low pH virus inactivation unit operation, for example a neutralized virus inactivated pool or eluate.

Advantageously, the chromatography columns located in the skids 104, 106 discussed above with respect to the processes 200, 300 may be physically separate from one another, i.e., not connected in series or in any other manner. The chromatography columns 120 are cycled in parallel, with no column connectivity during loading (no column overloading), overflow from one column 120 is not loaded directly onto any another chromatography column in a separate skid. Utilizing the above method results in the columns 120 of the skids 104, 106 not being overloaded, as would be the result of a flow-through process between physically connected serial columns in systems such as periodic counter-current chromatography. As such, the methods described herein are particularly advantageous for recombinant proteins that have stability issues, such as on-column aggregation or aggregation at high concentration. The skids 104, 106 can include one or more of the followings aspects.

The chromatography column 120 in the skids 104, 106 can be a single chromatography column suitable for capture chromatography. Such chromatography columns make use of mediums, such as resins, membranes, gels and the like, to which, under suitable conditions, the recombinant protein of interest will bind to the chromatography medium. By "binding" the protein to the chromatography medium is meant exposing the protein of interest to the chromatography medium under appropriate conditions (pH, conductivity) or affinities such that the protein of interest is reversibly immobilized in or on the chromatography medium by virtue of interactions between the protein of interest and a charged group or charged groups of the chromatography medium, such as ion exchange medium, or ligands or other agents that have affinity for the protein of interest, such as Protein A medium.

Examples of chromatography modalities, such as affinity chromatography including Protein A, Protein G or Protein L chromatography, immobilized metal affinity chromatography (IMAC), size exclusion chromatography (SEC), ion exchange chromatography (IEX) including cation exchange chromatography (CEX), and anion exchange chromatography (AEX), hydrophobic interaction chromatography (HIC), multi modal chromatography or mixed modal chromatography (MM), hydroxyapatite chromatography (HA), and the like are suitable for use in the parallel chromatography system described herein. Such chromatography materials are known in the art and are commercially available.

Two or more similar chromatography column skids 104, 106 may be run in parallel and controlled by the continuous parallel chromatography system 100 as described herein. While at least one chromatography skid is executing the operation with the longest cycle time, e.g., the long step, (such as loading or elution), at least one chromatography skid is executing the production process cycle which includes at least one or more process steps with shorter cycle times, which can include one or more of the equilibration, loading, washing, elution, and column cleaning and regeneration steps, which may include column striping and flushing. The steps and the order, number and duration of the steps is influenced by the protein being purified and the objectives of the manufacturing campaign.

The chromatography column skids 104, 106 can also include at least one pump 122, 124. In one embodiment, the skid includes two or more pumps. The pump(s) are used to push the feed load through the chromatography column, particularly at a constant flow rate. Such pumps include, for example, peristaltic, diaphragm, and centrifugal pumps. For skids equipped with a single pump, timed valve switching can be used to manage metered liquid solutions from two or three inlet channels. For skids with two or more pumps, independent pumps can be connected to the inlets.

Each chromatography column skid 104, 106 includes at least one inlet and one outlet to direct the flow of the feed into the column and eluate out of the column. The inlet may be selectively coupled to an upstream source. The upstream source can include any fluids that are to be fed into the chromatography skid, i.e., feedstocks. The upstream source may be contained in surge tanks, holding tanks, bags, or other suitable containers adapted to provide a feed to at least one chromatography column skid.

The feedstock comprises any fluid that is fed onto the chromatography column. The feedstock may include at least one protein of interest. The feedstock may originate from pool material collected in surge tanks, holding tanks, bags, or other suitable containers adapted for such collection and storage. Such vessels may be adapted to provide the feedstock to the chromatography column skids. The feedstock may also be in the form of an eluate stream direct from an upstream source.

In some instances, feedstocks can include harvested cell culture fluid comprising a protein of interest that has been collected in a pool or in an eluate stream. The harvested cell culture fluid may be collected from any type of harvest unit operation. The feedstock may comprise an eluant pool or stream collected from a chromatography column that comprises a protein of interest. The chromatography column eluate pool or stream can be collected from any type of capture chromatography unit operation. Examples of chromatography column pools or streams include affinity chromatography column eluant pools, such as from a Protein A, Protein G or Protein L. The chromatography pool or stream may be an immobilized metal affinity chromatography eluant pool or stream. The chromatography column pool may be an ion exchange chromatography eluant pool or stream, such as an anion exchange chromatography eluant pool or stream or a cation exchange chromatography eluant pool or stream, a multi-modal or mixed modal chromatography eluant pool or stream, a hydrophobic interaction chromatography column eluant pool or stream, a hydroxyapatite column eluant pool or stream, or a size exclusion chromatography column eluant pool or stream comprising the protein component, for example.

The feedstock may include a virus inactivated eluate pool or stream from any of the above. The feedstock may also include a neutralized virus inactivated eluant pool or stream from any of the above. The feedstock may also include a neutralized eluate pool or stream from any of the above. The feedstock may include a viral filtered eluate pool or stream from any of the above.

A feedstock may also include one or more "processing feedstocks", such as stock solutions, salt solutions, acid solutions, buffer solutions, and combinations thereof and the like suitable for use for equilibrating, washing, eluting, reconstituting, stripping, and/or flushing the chromatography column on the skid.

One or more sensors can be located at the inlet and/or outlet for measuring and/or monitoring such physical parameters as flow rate, pressure, and/or volume of the feedstock into and out of the skid. Sensors may also be used to monitor/measure the quality/quantity of the protein of interest, contaminants, and/or impurities in the eluate. Sensors may also be used to monitor/measure the efficacy of equilibration, wash, reconstitution, strip and/or flush steps. The sensors may include UV sensors and pH sensors.

Each chromatography column skid 104, 106 can include a plurality of valves.

Each chromatography column skid 104, 106 includes the structures and supports to house and operate the components that make up the skids 104, 106, such as the chromatography columns, pumps, inlet and outlets, sensors, valves, filters, and so forth. The skid structure may be made from any suitable material, such as stainless steel, aluminum, and/or plastics that are suitable for the purpose and use, particularly use in a controlled environment. The skids may have some mechanism for movement, such as wheels or rollers.

Figure 6:
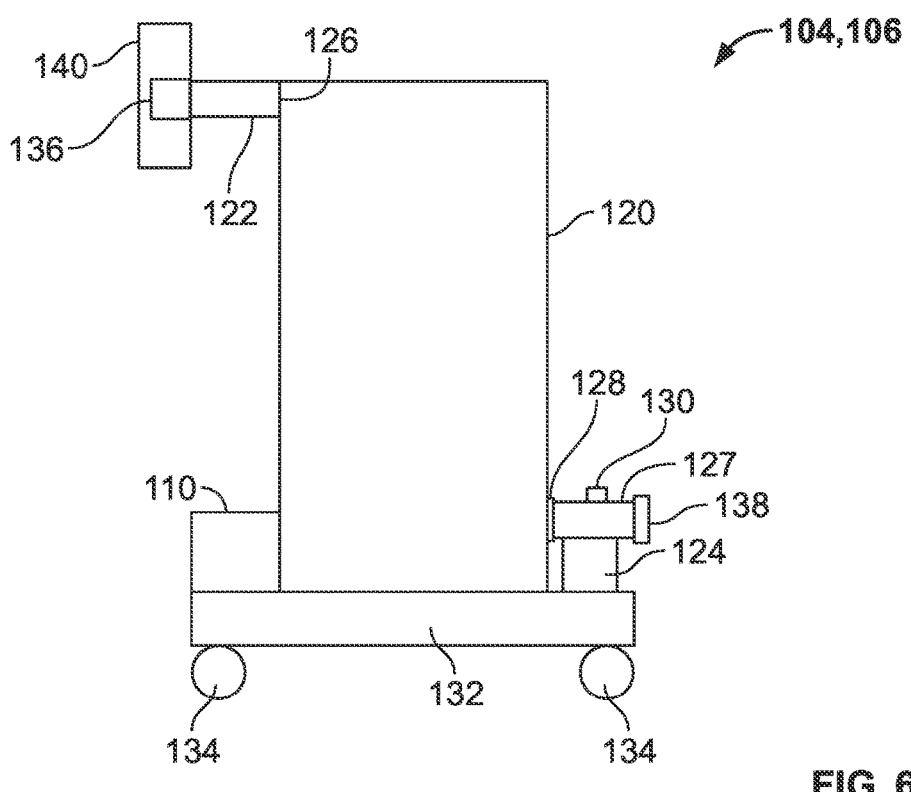
FIG. 6 is a diagrammatic view of an example chromatography skid for the parallel process chromatography system of FIG. 1.

An exemplary chromatography skid 104, 106 is shown in FIG. 6. The chromatography skid 104, 106 may comprise a) any number of inlet valves 136, arranged on at least two inlet valve manifolds 140, b) at least one pump 122, 124, c) a single chromatography column 120 with appropriate valving 136 to be bypassed or selected for the flow path, d) at least one instrument 130 capable of sensing the recombinant protein of interest as it is loaded and/or eluted from the column, and e) any number of outlet valves 138 for direction of feedstock and waste streams into suitable holding vessels, waste vessels, and/or to direct an eluate stream to other downstream processing units. Skids 104, 106 could also include additional valving, filters, and instrumentation for measurement of pressures, flows, pH, conductivity, temperature or the like. Additionally, the skid 104, 106 may have a bubble trap for the entrapment of air in the feedstock load stream or buffer inlets. The addition of separate sampling mechanisms or safety mechanisms for pressure relief may also be included on the skid 104, 106, without affecting its ability to participate in the parallel chromatography system 100.

In the illustrated form, each skid 104, 106 includes components suitable for independent batch processing. As such, each skid 104, 106 includes a chromatography column 120, a pump 122, an optional second pump 124, an inlet 126, an outlet 127, at least one filter 128, and an outlet sensor 130. Moreover, all of the components can be installed on a base 132 having wheels/rollers 134 that allow the skids 104, 106 to be easily maneuvered within a facility to a desired location. This allows a user to easily set up any desired number of skids 104, 106 as required for a manufacturing campaign. Fluid flow to the inlet 126 of each of the skids 104, 106 can be controlled by operation of one or more valves 136, which can be carried by the respective skid 104, 106 or can be located upstream of the skids 104, 106, as desired, and fluid flow to the outlet 127 of each of the skids 104, 106 can be controlled by operation of one or more valves 138, which can be carried by the respective skid 104, 106 or can be located downstream of the skids 104, 106. So configured, when the valve 136 for one of the skids 104, 106 is opened, a predetermined amount of feedstock containing a protein of interest is loaded onto the column 120 in bind and elute mode. The output from the column can be controlled by the valve 138 and measured by the outlet sensor 130, in particular, the measurement can be used to determine when the elution has a desired quality. For example, the outlet sensor 130 can be an ultraviolet (UV) sensor to determine protein concentrations. Advantageously, the system 100 can utilize single-use columns, which allow the column 120 to be replaced between uses. The columns 120 of the skids 104, 106 in the system can also having varying sizes/volumes with respect to one another.

The loading and processing steps may be performed using a single pump 122 and timed switching of the valves 136 to manage metered liquid solutions from two or three inlet channels.

The loading and processing steps may be performed using two or more pumps 122, 124 configured to allow separate operation of each pump 122, 124. The central processor 108, or, alternatively, one of the individual processors 110, directs the actions of each pump 122, 124. As discussed above with reference to FIGS. 2-5, one or more pumps 122, 124 can be used to operate the primary cycle of the process 200, 300, the longest cycle that sets the timing for the system 100 (loading for affinity chromatography, eluting for polish chromatography, for example) and one or more pumps 122, 124 can be used to operate the secondary cycle, the production process cycle which includes at least one or more steps of equilibration, loading, washing, elution, and column cleaning and regeneration, which may include column striping and flushing.

The control circuit 102 synchronizes the actions of the two or more chromatography skids 104, 106. The control circuit 102 directs the skids 104, 106 as to which cycle to execute and, upon completion of the cycle, synchronizes the switch to execute the next cycle.

Figure 7:
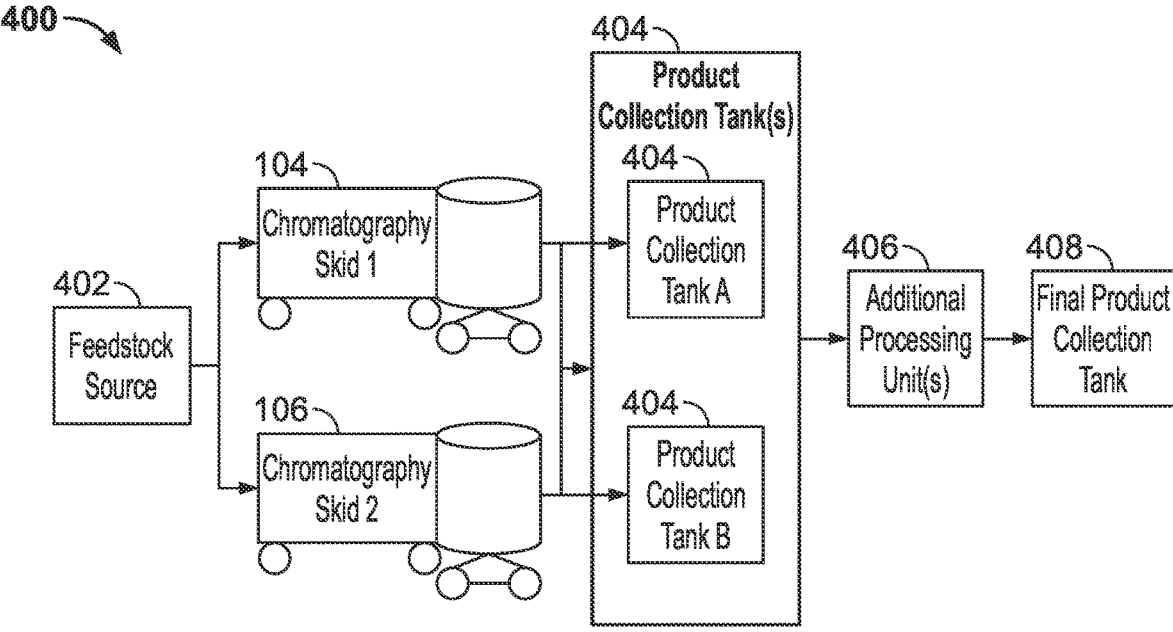
FIG. 7 is a diagrammatic view of a system incorporating the parallel process chromatography system of FIG. 1.

An example of a continuous process chromatography system 400 configuration is shown in FIG. 7 which includes a feedstock source 402, which provides a feedstock to be loaded on to the chromatography column skids 104, 106. Elution from the skids 104, 106 is fed to one or more collection tanks 404. For example, the collection tank 404 can be a shared common tank for each of the skids, each skid can have a separate collection tank, or groups of skids can share separate tanks. For configurations utilizing a shared collection tank 404, the tank 404 can operate as a surge tank to maintain continuous processing of the entire system regardless of which skid 104, 106 is processing feedstock at any given moment. The collection tank 304 then fluidly connects to downstream processing units 406 and ultimately a final product collection tank 408.

Figures 8, 9, 10:
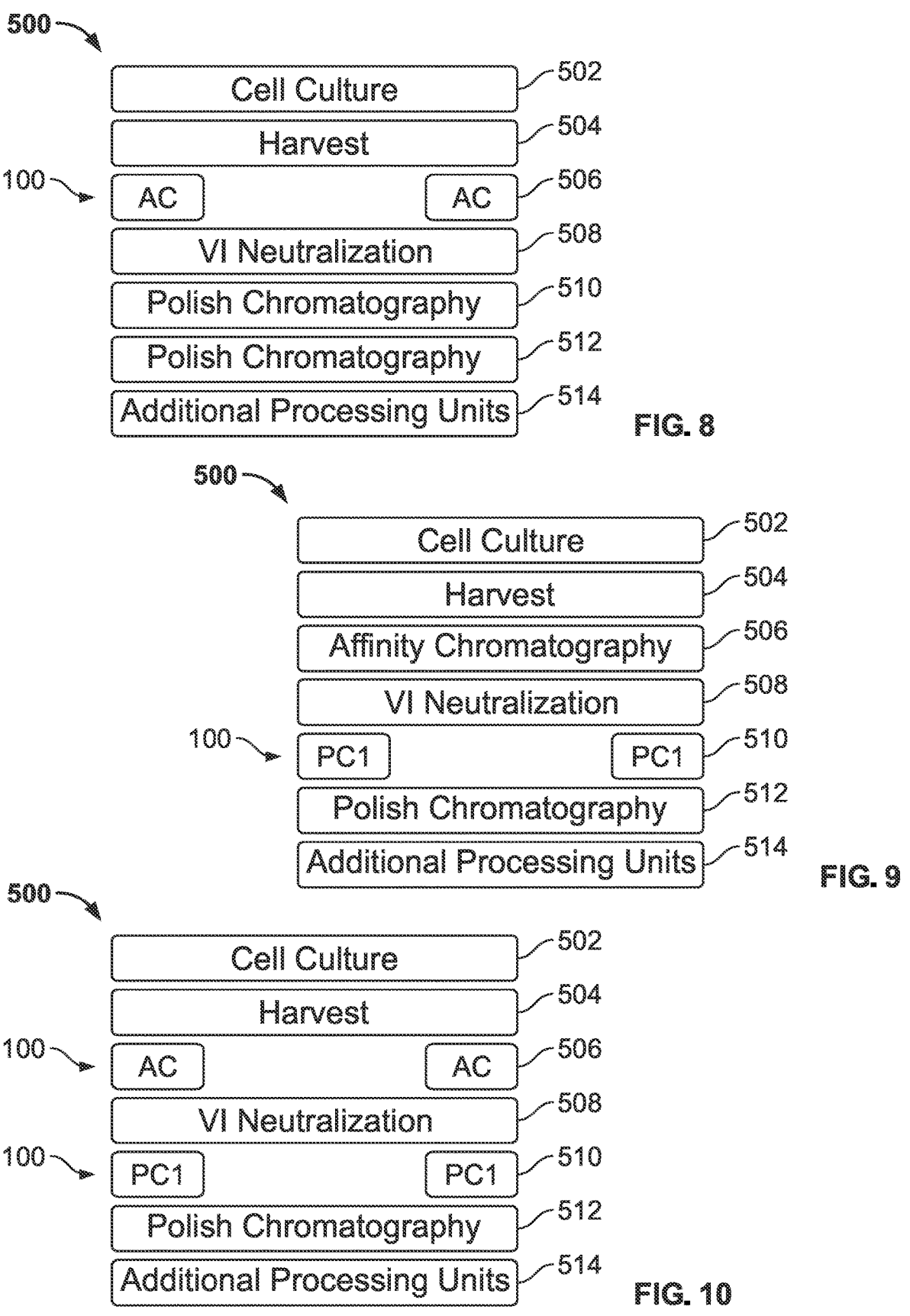
FIG. 8 is a diagrammatic view of a first exemplary configuration for using parallel process chromatography in a downstream process.
FIG. 9 is a diagrammatic view of a second exemplary configuration for using parallel process chromatography in a downstream process.
FIG. 10 is a diagrammatic view of a third exemplary configuration for using parallel process chromatography in a downstream process.

FIGS. 8-10 show several exemplary configurations that incorporate the continuous processing chromatography processes described herein into a recombinant protein manufacturing process 500. The process 500 begins with a cell culture operation 502, followed by a harvest operation 504, an affinity chromatography operation 506, a virus inactivation and neutralization operation 508, and first and second polish chromatography operations 510, 512. Finally, the process 500 can continue to additional processing unit operations 514.

In the downstream process 500 of FIG. 8, at least two affinity chromatography skids (AC) 104, 106 are utilized to operate in the parallel processing system 100 according to the process 200 described above with respect to FIGS. 2 and 3 in the affinity chromatography operation 506 following the harvest operation 504. In this form, the polish chromatography operations 510, 512 may be any number of single column independent units operations or two columns joined in series to form a single polish chromatography unit operation, for example.

In the downstream process 500 of FIG. 9, at least two polish chromatography skids (PC1) 104, 106 are utilized to operate in the parallel processing system 100 according to the process 300 described above with respect to FIGS. 4 and 5 in the first polish chromatography operation 510 following the affinity chromatography operation 506 and the virus inactivation and neutralization operation 508 of the affinity chromatography eluate. In this form, the affinity chromatography operation 506 and the second polish chromatography operation 512 can be performed by any number of single independent chromatography unit operations. In one aspect, the order of the polish chromatography steps 510 and 512 can be reversed, with the polish chromatography operation performed using the parallel processing system 100 taking place as the second polish chromatography operation. In one aspect, the polish chromatography operation 510 may also be the only polish operation. In one aspect, there may be more than one polish chromatography operation 510 and/or 512.

In the downstream process 500 of FIG. 10, at least two affinity chromatography skids (AC) 104, 106 are utilized to operate in the parallel processing system 100 according to the process 200 described above with respect to FIGS. 2 and 3 in the affinity chromatography operation 506 following the harvest operation 504. Further, at least two polish chromatography skids (PC1) 104, 106 are utilized to operate in the parallel processing system 100 according to the process 300 described above with respect to FIGS. 4 and 5 in the first polish chromatography operation 510 following the affinity chromatography operation 506 and the virus inactivation and neutralization operation 508 of the affinity chromatography eluate. In this form, the second polish chromatography operation 512 can be performed by any number of single independent chromatography unit operations. In one aspect, the order of the polish chromatography steps 510 and 512 can be reversed, with the polish chromatography operation performed using the parallel processing system 100 taking place as the second polish chromatography operation. In one aspect, the polish chromatography operation 510 may be the only polish operation. In one aspect, there may be more than one polish chromatography operation 510 and/or 512.

The timing of the loading and elution steps can be varied. For example, when performing affinity chromatography using Protein A affinity chromatography columns, the loading phase is preferably the longest cycle (see FIG. 3). When performing polish chromatography using cation exchange chromatography columns for example, the elution phase is preferably the longest cycle (See FIG. 5). However, the determination of the longest cycle for any unit operation performed using the parallel chromatography system 100 described herein can be made based on the protein to be purified, the manufacturing campaign objectives and/or any other desired parameter or goal of the process.

Figure 11:
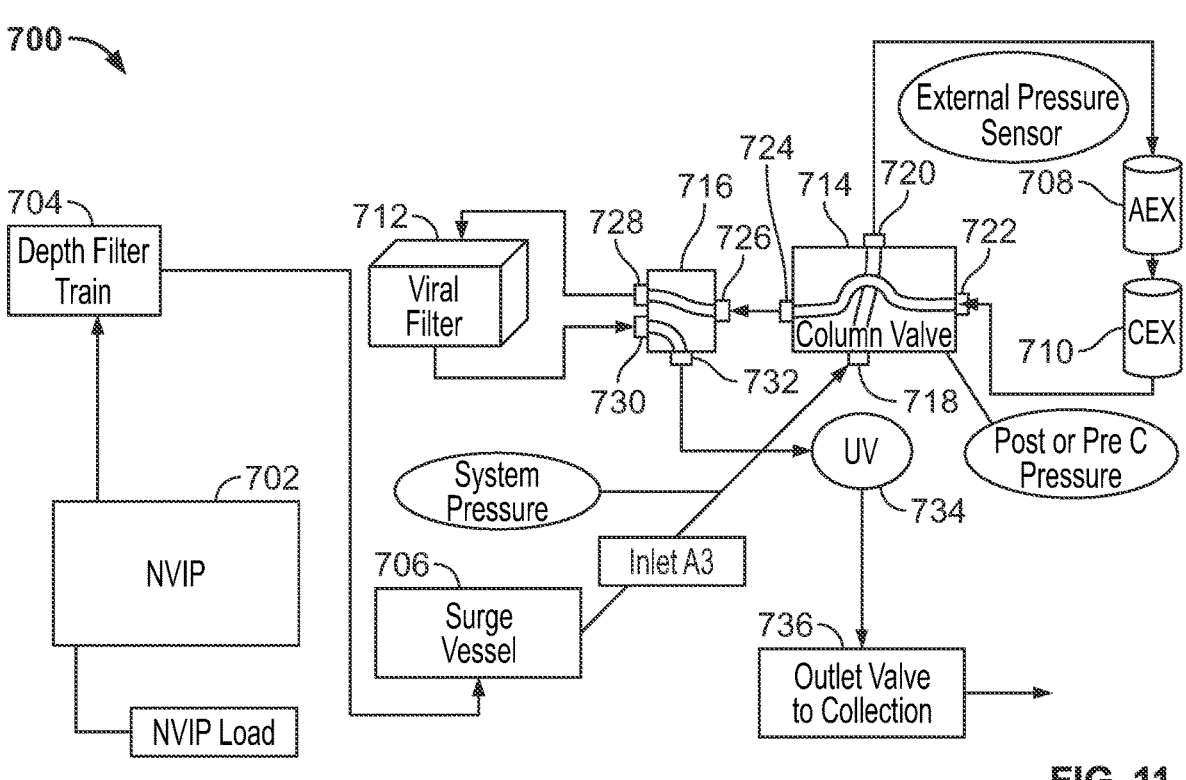
FIG. 11 is a diagrammatic view of a depth filtration, flow-through polishing, and virus filtration configuration.

A downstream process 700 is shown in FIG. 11 for processing of a neutralized virus inactivated pool (NVIP) 702. The NVIP 702 may be neutralized to a pH that is more compatible with at least one following downstream processing operations, for example. A depth filter train 704 is connected downstream of the NVIP 702 and the permeate from the depth filter train 704 can be collected in a surge vessel 706.

The surge vessel 706 can then be used to supply flow-through polishing and virus filtration (VF) processing operations. As shown, the exemplary polishing and virus filtration processing operations include an anion exchange chromatography column (AEX) 708 directly connected to a cation exchange chromatography column (CEX) 710 in a flow-through configuration, and a viral filter 712. In one embodiment, the viral filter 712 can include a pre-filter and a virus filter.

A column valve 714 and a common valve 716 controls fluid flow to the various components of the process 700. Pursuant to this, the column valve 714 can include a plurality of ports, including a feed inlet port 718, a column inlet port 720, a column outlet port 722, and a feed outlet port 724. Similarly, the common valve 716 can include a plurality of ports, including a feed inlet port 726, a VF inlet port 728, a VF outlet port 730, and a feed outlet port 732.

With this configuration, the surge vessel 706 can be fluidly connected to the AEX column 708 via the feed inlet port 718 and the column inlet port 720 of the column valve 714. Further, the CEX column 710 can be fluidly connected to the viral filter 712 via the column outlet port 722 and the feed outlet port 732 of the column valve 714 and the feed inlet port 726 and VF inlet port 728 of the common valve 716. Finally, feed from the viral filter 712 can be supplied to a UV monitor 734 via the VF outlet port 730 and the feed outlet port 732 of the common valve 716. Feed from the UV monitor 734 can then be supplied to an outlet valve 736 and ultimately one or more collection vessels.

Manufacturing recombinant proteins using cell culture processes carries an inherent risk of transmitting viral contaminants. Such contaminants can come from many sources, including starting materials, reagents (particularly reagents of animal origin), and contamination of the manufacturing system due to failures in the GMP process. As such, regulatory authorities recommend that biomanufacturing processes have dedicated virus inactivation and virus removal steps and request manufacturers validate the removal and inactivation of viruses from all biological products.

Enveloped viruses are typically inactivated. Non-enveloped viruses are more difficult to inactivate without risk to the protein therapeutic being manufactured; however such viruses can be removed by size-based filtration methods, such as by removing virus particles using filters with small pore sizes. Viral filtration can be performed using micro- or nano-filters, such as those available from Asahi Kasei (Planova®) and EDM Millipore (VPro®).

Virus inactivation refers to a process where enveloped virus is modified such that it can no longer infect cells, replicate, and/or propagate. Various methods can be employed for virus inactivation and include heat inactivation/pasteurization, UV and gamma ray irradiation, use of high intensity broad spectrum white light, addition of chemical inactivating agents, surfactants and solvent/detergent treatments. In one embodiment, virus inactivation is accomplished by incubation at low pH, which is very effective in specifically inactivating enveloped viruses.

Low pH viral inactivation can be performed in batch mode that includes a low pH hold for a defined duration and temperature. Virus inactivation can be combined with capture chromatography by washing the bound capture chromatography columns under low pH/high salt conditions. Eluting a capture chromatography column under conditions suitable for virus inactivation have been performed using extra buffer volumes (which adds cost, extends purification time, and may result in protein loss) and using elution buffers with much lower pH (which may impact protein integrity, especially with multi-component engineered proteins), and/or higher buffer concentrations.

Development of in-line, continuous low pH inactivation methods have focused on use of equipment and methods for performing the task, such as coiled flow invertors or other mechanisms that maintain fluid flow for a minimum residence time under target low pH conditions. However, the nature of the buffers and titrants used to affect the pH change and neutralization have largely been ignored. Typically, low pH viral inactivation has been performed using acetate buffer (pKa 4.8) and Tris Base (pKa 8.1) to affect the desired pH changes.

Making use of a concentrated solution of Tris Base (>1 M) may reduce the dilution during the neutralization but can be difficult to control with automation and/or in-line conditioning strategies. Further, the high concentration of the buffer increases the chances for over-titration. The titrant concentration, pKa, and composition dictates the sensitivity to volume changes (over/under addition) which is critical for highly automated and/or in-line titration processes, particularly those used in semi-continuous and continuous unit operations and/or manufacturing processes, including the parallel processing system described herein. Over titration can damage the product of interest via deamidation, oxidation, or other degradation mechanisms, thus risking the quality of the purified protein and/or the entire batch/lot being processed.

It was found that making use of elution buffers during capture chromatography unit operations, such as Protein A, that have a pKa lower by more than 1 pH unit than the neutralization target pH (i.e., the elution buffer does not buffer at the target pH for the neutralization) was suitable for controlling in-line, continuous, low pH viral inactivation. As described herein, particularly in the Examples below, eluting a capture chromatography column using a low pKa acid such as formic, phosphoric, or other acids with a pKa less than or equal to 4, resulted in a virus inactivated elution pool with a pH of 3.6±0.1. This was an effective elution/virus inactivation strategy that minimized buffer volume at an effective pH. There was also an interdependence between the elution buffer pH, elution buffer concentration, and pool collection volume. At a target elution buffer concentration of 100 mM, a buffer pH range of pH 3.3 to pH 3.5, and pool collection volumes ranging from 2.75 CV to 4.25 CV, resulted in the desired target pH range of 3.6±0.1. Collected pool volumes, the type and amount of neutralization buffer, and pool protein concentration can be optimized by varying the elution buffer pH and concentration, enabling pool volumes up to 7.7 CV and as low as 2.1 CV.

In one embodiment, the invention provides a viral inactivation pool obtained by eluting an affinity chromatography column using an elution buffer having a pKa more than 1 pH unit lower than the neutralizing target pH. In one embodiment, the virus inactivation pool is obtained by eluting an affinity chromatography column using a buffer comprising an acid having a pKa below 4 resulting in a virus inactivated elution pool with a pH of 3.6±0.1. In one embodiment the pH of the buffer is 3.3 to 3.6. In one embodiment the pH of the buffer is 3.3 to 3.5. In one embodiment the pH of the buffer is 3.3 to 3.4. In one embodiment the pH of the buffer is 3.3 to 3.6. In one embodiment the pH of the buffer is 3.4 to 3.5. In one embodiment the pH of the buffer is 3.5 to 3.6. In one embodiment the pH of the buffer is 3.3±0.1, 3.4±0.1, 3.5±0.1 or 3.6±0.1. In one embodiment the pH of the buffer is 3.4±0.1. In one embodiment, an acid having a pKa below 4 includes formic acid and phosphoric acid. In one embodiment, the acid is 100 mM formic acid at pH 3.4 to achieve a final viral inactivation pool pH of 3.6±0.1. In one embodiment of the invention the affinity chromatography is Protein A, Protein G, Protein A/G, or Protein L affinity chromatography. In one embodiment the elution collection volume is 2.1 CV to 7.7 CV. In one embodiment the elution collection volume is 2.1 CV to 4.25 CV. In one embodiment the elution collection volume is 2.1 CV to 2.75 CV. In one embodiment the elution collection volume is 2.75 CV to 4.25 CV. In one embodiment the elution collection volume is 2.75 CV to 7.7 CV. In one embodiment the elution collection volume is 4.25 CV to 7.7 CV. In one embodiment the elution collection volume is greater than or equal to 2.1 CV, 2.75, 3.5 CV, or 4.25 CV. In one embodiment the elution collection volume is 3.5 CV.

The viral inactivation elution pool may be mixed to ensure the entire pool is at the desired pH. The elution pool may be contained in disposable bags, surge tanks, storage tanks, or other appropriate containers. In one embodiment the elution pool container has a volume which is 10× to 4× smaller than the harvest storage container. In one embodiment the elution pool container has a volume which is 10× to 5× smaller than the harvest storage container. In one embodiment the elution pool container has a volume which is 10× to 6× smaller than the harvest storage container. In one embodiment the elution pool container has a volume which is 10× to 7× smaller than the harvest storage container. In one embodiment the elution pool container has a volume which is 10× to 8× smaller than the harvest storage container. In one embodiment the elution pool container has a volume which is 10× to 9× smaller than the harvest storage container. In one embodiment the elution pool container has a volume which is 9× to 4× smaller than the harvest storage container. In one embodiment the elution pool container has a volume which is 9× to 5× smaller than the harvest storage container. In one embodiment the elution pool container has a volume which is 9× to 6× smaller than the harvest storage container. In one embodiment the elution pool container has a volume which is 9× to 7× smaller than the harvest storage container. In one embodiment the elution pool container has a volume which is 9× to 8× smaller than the harvest storage container. In one embodiment the elution pool container has a volume which is 8× to 4× smaller than the harvest storage container. In one embodiment the elution pool container has a volume which is 8× to 5× smaller than the harvest storage container. In one embodiment the elution pool container has a volume which is 8× to 6× smaller than the harvest storage container. In one embodiment the elution pool container has a volume which is 8× to 7× smaller than the harvest storage container. In one embodiment the elution pool container has a volume which is 7× to 4× smaller than the harvest storage container. In one embodiment the elution pool container has a volume which is 7× to 5× smaller than the harvest storage container. In one embodiment the elution pool container has a volume which is 7× to 6× smaller than the harvest storage container. In one embodiment the elution pool container has a volume which is 6× to 4× smaller than the harvest storage container. In one embodiment the elution pool container has a volume which is 6× to 5× smaller than the harvest storage container. In one embodiment the elution pool container has a volume which is 5× to 4× smaller than the harvest storage container.

The viral inactivation may occur over a predetermined time. One aspect of the invention provides that an elution pool is subjected to a low pH condition for at least 30 minutes or longer, prior to neutralization. In one embodiment the elution pool is subjected to a low pH condition for 24 hours or more. In one embodiment the elution pool is subjected to a low pH condition for at least 30 minutes to about 24 hours. In one embodiment the elution pool is subjected to a low pH condition for at least 1 hour to about 24 hours. In one embodiment the elution pool is subjected to a low pH condition for at least 2 hours to about 24 hours. In one embodiment the elution pool is subjected to a low pH condition for at least 3 hours to about 24 hours. In one embodiment the elution pool is subjected to a low pH condition for at least 4 hours to about 24 hours. In one embodiment the elution pool is subjected to a low pH condition for at least 5 hours to about 24 hours. In one embodiment the elution pool is subjected to a low pH condition for at least 6 hours to about 24 hours. In one embodiment the elution pool is subjected to a low pH condition for at least 10 hours to about 24 hours. In one embodiment the elution pool is subjected to a low pH condition for at least 12 hours to about 24 hours. In one embodiment the elution pool is subjected to a low pH condition for at least 15 hours to about 24 hours. In one embodiment the elution pool is subjected to a low pH condition for at least 18 hours to about 24 hours. In one embodiment the elution pool is subjected to a low pH condition for at least 30 minutes to at least 6 hours. In one embodiment the elution pool is subjected to a low pH condition for at least 30 minutes to at least 5.5 hours. In one embodiment the elution pool is subjected to a low pH condition for at least 30 minutes to at least 5 hours. In one embodiment the elution pool is subjected to a low pH condition for at least 30 minutes to at least 4.5 hours. In one embodiment the elution pool is subjected to a low pH condition for at least 30 minutes to at least 4 hours. In one embodiment the elution pool is subjected to a low pH condition for at least 30 minutes to at least 3.5 hours. In one embodiment the elution pool is subjected to a low pH condition for at least 30 minutes to at least 3 hours. In one embodiment the elution pool is subjected to a low pH condition for at least 30 minutes to at least 2.5 hours. In one embodiment the elution pool is subjected to a low pH condition for at least 30 minutes to at least 2 hours. In one embodiment the elution pool is subjected to a low pH condition for at least 30 minutes to at least 1.5 hours. In one embodiment the elution pool is subjected to a low pH condition for at least 30 minutes to at least 1 hour. In one embodiment the elution pool is subjected to a low pH condition for at least 1 hour to at about 2 hours. In one embodiment the elution pool is subjected to a low pH condition for at least 1 hour to at least 1.5 hours. In one embodiment the elution pool is subjected to a low pH condition for at least 1.5 hours to about 2 hours. In one embodiment the elution pool is subjected to a low pH condition for at least 30 minutes. In one embodiment the elution pool is subjected to a low pH condition for at least 1 hour. In one embodiment the elution pool is subjected to a low pH condition for at least 1.5 hours. In one embodiment the elution pool is subjected to a low pH condition for at least 2 hours. In one embodiment the elution pool is subjected to a low pH condition for at least 1, 2, 3, 4, 5, 6, 7, 8, 9, 10, 11, 12, 13, 14, 15, 16, 17, 18, 19, 20, 21, 22, 23, or 24 hours.

In some forms, the viral inactivation process may be automated.

The viral inactivated pool may be neutralized, (neutralized virus inactivated pool (nVIP)), to a pH that is more compatible with at least one following downstream processing operation. Typical neutralization processes use high concentration buffers, such as 1 M Tris, to titrate the pool to the desired target pH. For example, when using 1 M Tris, the pH increases rapidly which is desirable for batch mode with a fixed tank volume. For finer control, reducing the Tris concentration to 0.5 M slows the pH change, but at the cost of requiring a greater buffer volume to achieve same target pH. For a continuous process, without a limiting tank volume, excess buffer may be acceptable. However, the desire to reduce cost and dematerialize manufacturing processes is driving the move to smaller facility sizes and the corresponding use of minimal equipment and materials, which have led to neutralizing buffer volumes becoming a limiting factor in some manufacturing processes. Compression of manufacturing processes to minimize buffer exchange and conditioning while maintaining high throughput and productivity would be beneficial, particularly in combination with the parallel process system described herein.

An effective neutralization strategy was developed that allows reasonable control over buffer volumes typical of a small-scale process, without increasing the conductivity of the neutralization pool above 10 mS/cm. This neutralization buffer system comprises a titrant that does not have buffering capacity in the target pH range, buffering capacity being defined as having a pKa within ±1 pH unit of target pH, such as sodium acetate, in combination with a background buffering species which buffers at the desired pH, such as Tris Base. This background buffer helps prevent over titration due to excess addition of titrant.

Provided herein is a neutralizing buffer system capable of minimizing volume expansion of the viral inactivated eluate pool while maintaining conductivity less than or equal to 10 mS/cm. The neutralizing buffer system can include a titrant that does not have buffer capacity in the target pH range and a buffering agent which buffers at a desired pH. In addition, when this neutralization buffer system is used in combination with capture elution conditions having an acid with a pKa below 4 to a pool pH of less than 3.7, it minimizes buffer change downstream and contributes to improved throughput while maintaining purification performance. Use of this VI/neutralization strategy for smaller volume systems enables the purification of proteins in manufacturing processes that make use of minimal equipment and facility size.

The neutralizing buffer can be added to the virus inactivated elution pool in a mixing vessel, mixed in-line using a static mixer, or by any other suitable methods. The resulting neutralized virus inactivated pool can be stored as a pool, combined with other pools, and/or processed forward in a semi-continuous, continuous or contiguous manner. A virus inactivation and neutralization unit operation can be automated, including timed virus inactivation, followed by neutralization using a ratio of virus inactivation pool to neutralization buffer flow through a static mixer.

The neutralizing buffer system can include a titrant having a pKa greater than the target pH. In one embodiment, the titrant has a pKa greater than 7. In one embodiment the titrant is a base. In one embodiment of the invention the titrant is selected from citric acid, glutamic acid, and sodium acetate. In one embodiment of the invention the titrant is sodium acetate. In one embodiment of the invention titrant is sodium acetate at a concentration of less than 0.3 M. In one embodiment the titrant is sodium acetate at a concentration of greater than 0.1 M to less than 0.3 M. In one embodiment the titrant is sodium acetate at a concentration of 0.17 M to less than 0.3 M. In one embodiment the titrant is sodium acetate at a concentration of 0.238 M to less than 0.3 M. In one embodiment the titrant is sodium acetate at a concentration of greater than 0.1M to 0.238 M. In one embodiment the titrant is sodium acetate at a concentration of 0.17 M to 0.238 M. In one embodiment the titrant is sodium acetate at a concentration of greater than 0.1 M, 0.17M, 0.238M, or less than 0.3M.

The neutralizing buffer system can include a buffering agent having a pKa of 4.5 to 6.0. In one embodiment the buffering agent has a pKa of 4.5 to 5.5. In one embodiment the buffering agent has a pKa of 4.5 to 5.0. In one embodiment the buffering agent has a pKa of 5.0 to 5.5. In one embodiment the buffering agent has a pKa of 5.0 to 6.0. In embodiment the buffering agent has a pKa of 5.5 to 6.0. In one embodiment the buffering agent has a pKa of 4.5, 5.0, 5.5, or 6.0.

The neutralizing buffer system can include a buffering agent that is selected from 2-(N-morpholino)ethanesulfonic acid (MES), (3-(N-morpholino)propanesulfonic acid) (MOPS), (4-(2-hydroxyethyl)-1-piperazineethanesulfonic acid) (HEPES), and Tris Base. The neutralizing buffer system can include a buffering agent that is Tris Base. In one embodiment the neutralizing buffer system can include a buffering agent having a concentration of less than 0.2 M Tris Base. In one embodiment the buffering agent has a Tris Base concentration of less than 0.00005 M to less than 0.2 M. In one embodiment the buffering agent has a Tris Base concentration of 0.1075 M to less than 0.2 M. In one embodiment the buffering agent has a Tris Base concentration of 0.11 M to less than 0.2 M. In one embodiment the buffering agent has a Tris Base concentration of 0.115 M to less than 0.2 M. In one embodiment the buffering agent has a Tris Base concentration of 0.185 M to less than 0.2 M. In one embodiment the buffering agent has a Tris Base concentration of 0.1075 M to 0.185 M. In one embodiment the buffering agent has a Tris Base concentration of 0.11 M to 0.185 M. In one embodiment the buffering agent has a Tris Base concentration of 0.115 M to 0.185 M. In one embodiment the buffering agent has a Tris Base concentration of 0.1075 M to 0.115 M. In one embodiment the buffering agent has a Tris Base concentration of 0.11 M to 0.115 M. In one embodiment the buffering agent has a Tris Base concentration of 0.00005 M, 0.1075 M, 0.11M, 0.115 M, 0.185 M, or less than 0.2M.

The neutralizing buffer system can include a titrant having a pKa greater than 7 and a buffering agent having a pKa of 4.5 to 6.0. In one embodiment the neutralizing buffer system can include a titrant having a pKa greater than 7 and a buffering agent having a pKa of 4.5 to 5.0. In one embodiment the neutralizing buffer system can include a titrant having a pKa greater than 7 and a buffering agent having a pKa of 4.5 to 5.5. In one embodiment the neutralizing buffer system can include a titrant having a pKa greater than 7 and a buffering agent having a pKa of 5.0 to 6.0. In one embodiment the neutralizing buffer system can include a titrant having a pKa greater than 7 and a buffering agent having a pKa of 5.0 to 5.5. In one embodiment the neutralizing buffer system can include a titrant having a pKa greater than 7 and a buffering agent having a pKa of 5.5 to 6.0. In one embodiment the neutralizing buffer system can include a titrant having a pKa greater than 7 and a buffering agent having a pKa of 4.5, 5.0, 5.5, or 6.0.

The neutralizing buffer system can include a titrant that is sodium acetate and a buffering agent that is Tris Base. In one aspect of the invention the neutralizing buffer system can include sodium acetate at a concentration of greater than 0.1 M to less than 0.3 M sodium acetate and Tris Base at a concentration of greater than 0.00005 M to less than 0.2 M Tris Base. In one embodiment the neutralizing buffer system can include sodium acetate at a concentration of 0.17 M to 0.238 M sodium acetate and Tris Base at a concentration of 0.1075 M to 0.185 M. In one embodiment the neutralizing buffer system can include 0.17 M sodium acetate and 0.1075 M Tris Base. In one embodiment the neutralizing buffer system can include 0.17 M sodium acetate and Tris Base concentration of 0.11 M to 0.115 M. In one embodiment the neutralizing buffer system can include 0.17 M sodium acetate and 0.1075 M Tris Base. In one embodiment the neutralizing buffer can include 0.238 M sodium acetate and 0.185 M Tris Base. In one embodiment the neutralizing buffer system can include 0.17 M sodium acetate and 0.11 M Tris Base. In one embodiment the neutralizing buffer system comprises 0.17 M sodium acetate and 0.115 M Tris Base.

Also provided herein is a neutralizing buffer system capable of minimizing volume expansion of a viral inactivated eluate pool while maintaining conductivity less than or equal to 10 ms/cm, comprising a titrant with a pKa greater than 7 and a buffering agent with a pKa in the range of 4.5 to 6.0.

Also provided herein is a neutralizing buffer system capable of minimizing volume expansion of a viral inactivated eluate pool while maintaining conductivity less than or equal to 10 ms/cm, comprising sodium acetate as a titrant at a concentration in the range of greater than 0.1 M to less than 0.3 M and Tris Base as a buffering agent at a concentration in the range of greater than 0.00005 M to less than 0.2 M.

Also provided herein is a neutralizing buffer system capable of minimizing volume expansion of a viral inactivated eluate pool while maintaining conductivity ≤10 ms/cm, comprising sodium acetate at a concentration in the range of 0.17 M to 0.238 M sodium acetate and Tris Base in the range of 0.1075 M to 0.0.185 M.

This neutralizing buffer system for use in a continuous flow process for purification of a protein of interest provides the additional benefit of reducing buffer requirements, such as buffer exchange and buffer conditioning, by generating a single buffer.

In one aspect of the invention neutralization is achieved by combining the virus inactivation pool with the neutralizing buffer system in a mixing vessel. In one aspect of the invention, the neutralizing buffer system and the virus inactivated elution pool can be mixed in-line using a static mixer.

The neutralized virus inactivated pool can be stored as a single pool, combined with other neutralized pools, or processed forward in a continuous or contiguous manner.

The neutralized virus inactivated pool may be further subjected to filtration, such as depth filtration, and/or sterile filtration, to remove any resulting turbidity or precipitation.

The terms "polynucleotide" or "nucleic acid molecule" are used interchangeably throughout and include both single-stranded and double-stranded nucleic acids, genomic DNA, RNA, mRNA, cDNA, or synthetic origin or some combination thereof which is not associated with sequences normally found in nature. The terms "isolated polynucleotide" or "isolated nucleic acid molecule" specifically refer to sequences of synthetic origin or those not normally found in nature. Isolated nucleic acid molecules comprising specified sequences may include, in addition to the sequences expressing the protein of interest, coding sequences for up to ten or even up to twenty other proteins or portions thereof or may include operably linked regulatory sequences that control expression of the coding region of the recited nucleic acid sequences, and/or may include vector sequences. The nucleotides comprising the nucleic acid molecules can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The terms "polypeptide" or "protein" are used interchangeably throughout and refer to a molecule comprising two or more amino acid residues joined to each other by peptide bonds. Polypeptides and proteins also include macromolecules having one or more deletions from, insertions to, and/or substitutions of the amino acid residues of the native sequence, that is, a polypeptide or protein produced by a naturally-occurring and non-recombinant cell; or is produced by a genetically-engineered or recombinant cell. Proteins comprise molecules having one or more deletions from, insertions to, and/or substitutions of the amino acid residues of the amino acid sequence of the native protein. Proteins include engineered proteins such as fusion proteins. Polypeptides and proteins include amino acid polymers in which one or more amino acids are chemical analogs of a corresponding naturally-occurring amino acid and polymers. Polypeptides and proteins are also inclusive of modifications including, but not limited to, glycosylation, lipid attachment, sulfation, gamma-carboxylation of glutamic acid residues, hydroxylation and ADP-ribosylation. Proteins can be secreted proteins, non-secreted proteins, intracellular proteins, membrane-bound proteins. Polypeptides and proteins of interest can be produced by prokaryotic and eukaryotic cell lines, such as recombinant animal cell lines, using cell culture methods and may be referred to as "recombinant proteins". The expressed protein(s) may be produced intracellularly or secreted into the culture medium from which it can be recovered and/or collected.

As used herein, the term "isolated" means (i) free of at least some other proteins or polynucleotides with which it would normally be found, (ii) is essentially free of other proteins or polynucleotides from the same source, e.g., from the same species, (iii) separated from at least about 50 percent of polypeptides, polynucleotides, lipids, carbohydrates, or other materials with which it is associated in nature, (iv) operably associated (by covalent or noncovalent interaction) with a polypeptide or polynucleotide with which it is not associated in nature, or (v) does not occur in nature. The term "isolated protein" or "isolated recombinant protein" refers to a polypeptide or protein of interest, that is purified away from proteins or polypeptides or other contaminants that would interfere with its therapeutic, diagnostic, prophylactic, research or other use.

Polypeptides and proteins can be of scientific and/or commercial interest, including proteins that exert a therapeutic effect by binding, stimulating, neutralizing, or in any way interacting with a target, particularly a target among those listed below, including targets derived therefrom, targets related thereto, and modifications thereof.

Included are antigen-binding proteins, that comprise an antigen-binding region or antigen-binding portion that has affinity for another molecule to which it binds (antigen). Antigen-binding proteins include antibodies, antibody fragments, antibody derivatives, antibody analogs as well as fusion proteins, engineered proteins and the like that comprise one or more antigen-binding regions or portions.

The term "antibody" includes reference to both glycosylated and non-glycosylated immunoglobulins of any isotype or subclass or to an antigen-binding region thereof that competes with the intact antibody for specific binding. Unless otherwise specified, antibodies include human, humanized, chimeric, multi-specific, monoclonal, and polyclonal. Antibodies include the IgG1-, IgG2-, IgG3-, and/or IgG4-types.

Also included are non-naturally occurring engineered proteins, such as multispecific proteins.

"Multispecific", "multispecific protein", and "multispecific antibody" are used herein to refer to proteins that are recombinantly engineered to simultaneously bind, neutralize, and/or interact with at least two different antigens or at least two different epitopes on the same antigen.

The most common and most diverse of the multispecific proteins are those that bind two antigens, referred to herein as "bispecific", "bispecific proteins", and "bispecific antibody". Bispecific proteins can be grouped in two broad categories: immunoglobulin G (IgG)-like molecules and non-IgG-like molecules. IgG-like molecules retain Fc-mediated effector functions, such as antibody-dependent cell mediated cytotoxicity (ADCC), complement-dependent cytotoxicity (CDC), and antibody-dependent cellular phagocytosis (ADCP), the Fc region helps improve solubility and stability and facilitate some purification operations. Non-IgG-like molecules are smaller, enhancing tissue penetration. Bispecific proteins are sometimes used as a framework for additional components having binding specificities to different antigens or numbers of epitopes, increasing the binding specificity of the molecule.

The formats for bispecific proteins, which include bispecific antibodies, are constantly evolving and include, but are not limited to, quadromas, knobs-in-holes, cross-Mabs, dual variable domains IgG (DVD-IgG), IgG-single chain Fv (scFv), scFv-CH3 KIH, dual action Fab (DAF), half-molecule exchange, KA-bodies, tandem scFv, scFv-Fc, dia-, tria- or tetrabodies, single chain proteins capable of binding multiple targets, single chain diabodies (scDiabodies), scDiabodies-CH3, triple body, miniantibody, minibody, TriBi minibody, tandem diabodies, scDiabody-HAS, Tandem scFv-toxin, dual-affinity retargeting molecules (DARTs), nanobody, nanobody-HSA, dock and lock (DNL), strand exchange engineered domain SEEDbody, Triomab, leucine zipper (LUZ-Y), molecules made using the XmAb® platform; Fab-arm exchange, DutaMab, DT-IgG, charged pair, Fcab, orthogonal Fab, IgG(H)-scFv, scFV-(H)IgG, IgG (L)-scFV, IgG(L1H1)-Fv, IgG(H)-V, V(H)-IgG, IgG(L)-V V(L)-IgG, KIH IgG-scFab, 2scFV-IgG, IgG-2scFv, scFv4-Ig, Zybody, DVI-Ig4 (four-in-one), Fab-scFv, scFv-CH-CL-scFV, F(ab')2-scFv2, scFv-KIH, Fab-scFv-Fc, tetravalent HCAb, scDiabody-Fc, diabody-Fc, intrabody, ImmTAC, HSABody, IgG-IgG, Cov-X-Body, scFv1-PEG-scFv2, trispecific antibodies, tetravalent bispecific antibodies.

Also included are redesigned or engineered antibodies such as antibody-drug conjugates, glycol-engineered anti-bodies, and polypeptides that contain at least a portion of an immunoglobulin that is sufficient to confer specific antigen binding to a target polypeptide.

Included are genetically engineered receptors such as chimeric antigen receptors (CARs or CAR-Ts), TRUCKS (Chimeric antigen receptors that redirect T cells for univer-sal cytokine-mediated killing), and armored CARs (de-signed to modulate an immunosuppressive environment) and T cell receptors (TCRs).

Also included are single chain bispecific antibody con-structs, bi-specific T cell engagers, single chain bispecific T cell engagers (BITE®), and half-life extended bispecific T cell engagers (HLE BiTE®) (see WO 99/54440; WO 2005/040220; WO 2008/119567; US 2014/0302037; US 2014/0308285; WO 2014/151910; WO 2015/048272; WO 2013/128027; WO2014/140358; and WO 2017/134140, among others).

Also included are modified proteins, such as proteins modified chemically by a non-covalent bond, covalent bond, or both a covalent and non-covalent bond. Also included are proteins further comprising one or more post-translational modifications which may be made by cellular modification systems or modifications introduced ex vivo by enzymatic and/or chemical methods or introduced in other ways.

Proteins may also include recombinant fusion proteins that can include, for example, a multimerization domain, such as a leucine zipper or a coiled coil. Terminal polypep-tides, such as c-Myc, His tags, the 'Flag' epitope, pegylation, and the like to improve expression and aid purification. Also included are proteins comprising all or part of the amino acid sequences of differentiation antigens (referred to as CD proteins) or their ligands or proteins substantially similar to either of these.

In some embodiments, proteins include colony stimulat-ing factors, such as granulocyte colony-stimulating factor (G-CSF). Such G-CSF agents include, but are not limited to, Neupogen® (filgrastim) and Neulasta® (pegfilgrastim). Also included are erythropoiesis stimulating agents (ESA), such as Epogen® (epoetin alfa), Aranesp® (darbepoetin alfa), Dynepo® (epoetin delta), Mircera® (methyoxy poly-ethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epo-etin theta), epoetin alfa, epoetin beta, epoetin zeta, epoetin theta, and epoetin delta, epoetin omega, epoetin iota, tissue plasminogen activator, GLP-1 receptor agonists, as well as the molecules or variants or analogs thereof and biosimilars of any of the foregoing.

In some embodiments, proteins include proteins that bind specifically to one or more CD proteins, HER receptor family proteins, cell adhesion molecules, growth factors, nerve growth factors, fibroblast growth factors, transforming growth factors (TGF), insulin-like growth factors, osteoin-ductive factors, insulin and insulin-related proteins, coagu-lation and coagulation-related proteins, colony stimulating factors (CSFs), other blood and serum proteins blood group antigens; receptors, receptor-associated proteins, growth hormones, growth hormone receptors, T-cell receptors; neu-rotrophic factors, neurotrophins, relaxins, interferons, inter-leukins, viral antigens, lipoproteins, integrins, rheumatoid factors, immunotoxins, surface membrane proteins, trans-port proteins, homing receptors, addressins, regulatory pro-teins, and immunoadhesins.

In some embodiments proteins include proteins that bind to one of more of the following, alone or in any combination: 5T4, 17-A, ADAM 17, AFP, alpha folate receptor, ART-4, BAGE, Brc-abl, B7-H3, B7-H6, CAIX, CAMEL, CAP-1, carbonic anhydrase IX, CASP-8, CDD27m, CD proteins including but not limited to CD3, CD4, CD5, CD7, CD8, CD19, CD20, CD22, CD25, CD30, CD33, CD34, CD38, CD40, CD44, CD44v7/8, CD70, CD79a, CD79b, CD123, CD133, CD138, CD171, and CD174, CDK4/m, cadherin 19, placental-cadherin(CDH3), P-cadherin, gpA33, B7H3, CEA, CLL-1, CSPG4, CT, Cyp-B, Dp-0, DDL3, EBV, HER receptor family proteins, including, for instance, HER2, HER3, HER4, and the EGF receptor, EGFRvIII, EGP2, EGP40, ELF40, ErbB2, EpCAM, EphA2, ETV6-AML1, FPA, fetal AchR, cell adhesion molecules, for example, LFA-1, Mol, p150,95, VLA-4, ICAM-1, VCAM, and alpha v/beta 3 integrin, growth factors, including but not limited to, for example, vascular endothelial growth factor ("VEGF"); VEGFR2, growth hormone, thyroid stimulating hormone, follicle stimulating hormone, luteinizing hor-mone, growth hormone releasing factor, parathyroid hor-mone, mullerian-inhibiting substance, human macrophage inflammatory protein (MIP-1-alpha), erythropoietin (EPO), nerve growth factor, such as NGF-beta, platelet-derived growth factor (PDGF), fibroblast growth factors, including, for instance, aFGF and bFGF, epidermal growth factor (EGF), Cripto, transforming growth factors (TGF), includ-ing, among others, TGF-α and TGF-β, including TGF-β1, TGF-β2, TGF-β3, TGF-β4, or TGF-β5, insulin-like growth factors-I and -II (IGF-I and IGF-II), des(1-3)-IGF-I (brain IGF-I), and osteoinductive factors, insulins and insulin-related proteins, including but not limited to insulin, insulin A-chain, insulin B-chain, proinsulin, and insulin-like growth factor binding proteins; (coagulation and coagulation-re-lated proteins, such as, among others, factor VIII, tissue factor, von Willebrand factor, protein C, alpha-1-antitrypsin, plasminogen activators, such as urokinase and tissue plas-minogen activator ("t-PA"), bombazine, thrombin, throm-bopoietin, and thrombopoietin receptor, colony stimulating factors (CSFs), including the following, among others, M-CSF, GM-CSF, and G-CSF, other blood and serum pro-teins, including but not limited to albumin, IgE, and blood group antigens, receptors and receptor-associated proteins, including, for example, flk2/flt3 receptor, obesity (OB) receptor, growth hormone receptors, and T-cell receptors; (x) neurotrophic factors, including but not limited to, bone-derived neurotrophic factor (BDNF) and neurotrophin-3, -4, -5, or -6 (NT-3, NT-4, NT-5, or NT-6); (xi) relaxin A-chain, relaxin B-chain, and prorelaxin, interferons, including for example, interferon-alpha, -beta, and -gamma, interleukins (ILs), e.g., IL-1 to IL-10, IL-1a, IL-1R, IL-11Ra, IL-13Ra2, IL-12, IL-15, IL-17, IL-23, IL-12/IL-23, IL-2Ra, IL1-R1, IL-6 receptor, IL-4 receptor and/or IL-13 to the receptor, IL-13RA2, or IL-17 receptor, IL-1RAP, HER2/neu, HLA-A, HPV, HSP70, HST-2, hTERT, iCD, IgE, Kappa, KIAA0205, LAGE, Lambda, LDLR/FUT, Lewis-Y, (xiv) viral antigens, including but not limited to, an AIDS envelope viral antigen, lipoproteins, calcitonin, glucagon, atrial natriuretic factor, lung surfactant, tumor necrosis factor-alpha and -beta, enkephalinase, FLT3, FRa, G250, GAGE, GC2, GD3, Glypican-3(GPC3), GNT-V, GP-100, HAGE, HBV, HCV, BCMA, IgKappa, ROR-1, ERBB2, mesothelin, RANTES (regulated on activation normally T-cell expressed and secreted), mouse gonadotropin-associated peptide, Dnase, FR-alpha, inhibin, and activin, integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, MIC (MIC-a, MIC-B), ULBP 1-6, EPCAM, addressins, regulatory proteins, immunoadhesins, antigen-binding proteins, somatropin, CTGF, CTLA4, eotaxin-1, MAGE, MAGE1, MAGE2B, MART-1, Melan-A, MC1R, MCSP, MUM-1, MUM-2, MUM-3, Mesothelin, MUC1, MUC16, myosin/m, NA88-A, NCAM, NKG2D ligands, NY-ESO-1, P15, p150 minor bcr-abl, PML/RARa, PRAME, PSA, PSCA, PAMA, RAGE, ROR1, RU1, RU2, SAGE, CEA, c-MET, Claudin-18, GPC-3, EPHA2, FPA, LMP1, MG7, NY-ESO-1, PSCA, ganglioside GD2, glanglioside GM2, BAFF, OPGL (RANKL), myostatin, Dickkopf-1 (DKK-1), Ang2, NGF, IGF-1 receptor, hepatocyte growth factor (HGF), TRAIL-R2, c-Kit, B7RP-1, PSMA, NKG2D-1, programmed cell death protein 1 and ligand, PD1 and PDL1, mannose receptor/hCGβ, hepatitis-C virus, mesothelin dsFv[PE38 conjugate, *Legionella pneumophila* (Ily), IFN gamma, interferon gamma induced protein 10 (IP10), IFNAR, TALL-1, thymic stromal lymphopoietin (TSLP), proprotein convertase subtilisin/Kexin Type 9 (PCSK9), stem cell factors, calcitonin gene-related peptide (CGRP), OX40L, a4p7, platelet specific (platelet glycoprotein Iib/IIIb (PAC-1), transforming growth factor beta (TFGβ), Zona pellucida sperm-binding protein 3 (ZP-3), TWEAK, platelet derived growth factor receptor alpha (PDGFRα), SART, SSX-1, SSX-2, SSX-3, Survivin, TAA, TAG72, TEL/AML1, TEMs, TPI, TRP-1, TRP-2, TRP-2/INT2, VEGFR2, WT1, sclerostin, and biologically active fragments or variants of any of the foregoing.

In another embodiment, proteins include abciximab, adalimumab, adecatumumab, aflibercept, alemtuzumab, alirocumab, anakinra, atacicept, axicabtagene ciloleucel, basiliximab, belimumab, bevacizumab, biosozumab, blinatumomab, brentuximab vedotin, brodalumab, cantuzumab mertansine, canakinumab, cetuximab, certolizumab pegol, conatumumab, daclizumab, denosumab, eculizumab, edrecolomab, efalizumab, epratuzumab, ertumaxomab, etanercept, evolocumab, floteuzmab, galiximab, ganitumab, gemtuzumab, golimumab, ibritumomab tiuxetan, infliximab, ipilimumab, lerdelimumab, lumiliximab, lxdkizumab, lymhomun, mapatumumab, motesanib diphosphate, muromonab-CD3, natalizumab, nesiritide, nimotuzumab, nivolumab, ocrelizumab, ofatumumab, omalizumab, oprelvekin, palivizumab, panitumumab, pasotuxizumab, pembrolizumab, pertuzumab, pexelizumab, ranibizumab, rilotumumab, rituximab, romiplostim, romosozumab, sargamostim, solitomab, targomiRs, tisagenlecleucel, tocilizumab, tositumomab, trastuzumab, ustekinumab, vedolizumab, visilizumab, volociximab, zanolimumab, zalutumumab, AMG211(MT111, Medi1565,), AMG330, AMG420, AMG-110, MDX-447, TF2, rM28, HER2Bi-aATC, GD2Bi-aATC, MGD006, MGD007, MGD009, MGD010, MGD011 (JNJ64052781), IMCgp100, indium-labeled IMP-205, xm734, LY3164530, OMP-305BB3, REGN1979, COV322, ABT112, ABT165, RG-6013 (ACE910), RG7597 (MEDH7945A), RG7802, RG7813 (RO6895882), RG7386, BITS7201A (RG7990), RG7716, BFKF8488A (RG7992), MCLA-128, MM-111, MM141, MOR209/ES414, MSB0010841, ALX-0061, ALX0761, ALX0141; BII034020, AFM13, AFM11, SAR156597, FBTA05, PF06671008, GSK2434735, MEDI3902, MEDI0700, MEDI7352 or variants or analogs thereof, as well as biosimilars of any of the foregoing.

The proteins may comprise as components of one or more of the proteins CD28, CD28T, OX40, 4-1BB/CD137, CD2, CD3 (alpha, beta, delta, epsilon, gamma, zeta), CD4, CD5, CD7, CD8, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CDI Ia/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF, TNFr, integrin, signaling lymphocytic activation molecule, BTLA, Toll ligand receptor, ICAM-1, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDI-Id, ITGAE, CD103, ITGAL, CDI-Ia, LFA-1, ITGAM, CDI-Ib, ITGAX, CDI-Ic, ITGBI, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, 41-BB, GADS, SLP-76, PAG/Cbp, CD19a, CD83 ligand, or fragments or combinations thereof.

Proteins encompass all of the foregoing and further include antibodies comprising 1, 2, 3, 4, 5, or 6 of the complementarity determining regions (CDRs) of any of the aforementioned antibodies or antibody binding proteins. Also included are variants that comprise a region that is 70% or more, especially 80% or more, more especially 90% or more, yet more especially 95% or more, particularly 97% or more, more particularly 98% or more, yet more particularly 99% or more identical in amino acid sequence to a reference amino acid sequence of a protein of interest. Identity in this regard can be determined using a variety of well-known and readily available amino acid sequence analysis software. Preferred software includes those that implement the Smith-Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include FASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by MasPar.

The polypeptides and proteins described herein can be produced by recombinant animal cell lines using cell culture methods and may be referred to as recombinant proteins or recombinant proteins of interest. The recombinant protein(s) may be produced intracellularly or secreted into the culture medium from which it can be recovered and/or collected.

Expression systems and constructs in the form of plasmids, expression vectors, transcription or expression cassettes that comprise at least one nucleic acid molecule as described above are also provided herein, as well host cells comprising such expression systems or constructs. As used herein, "vector" means any molecule or entity (e.g., nucleic acid, plasmid, bacteriophage, transposon, cosmid, chromosome, virus, virus capsid, virion, naked DNA, complexed DNA and the like) suitable for use to transfer and/or transport protein encoding information into a host cell and/or to a specific location and/or compartment within a host cell.

Vectors can include, but are not limited to, viral and non-viral vectors, non-episomal mammalian vectors. Vectors are often referred to as expression vectors, for example, recombinant expression vectors or cloning vectors. The vector may be introduced into a host cell to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art.

"Cell" or "Cells" include any prokaryotic or eukaryotic cell. Cells can be either ex vivo, in vitro or in vivo, either separate or as part of a higher structure such as a tissue or organ. Cells include "host cells", also referred to as "cell lines", which are genetically engineered to express a polypeptide of commercial or scientific interest. Host cells are typically derived from a lineage arising from a primary culture that can be maintained in culture for an unlimited time. Genetically engineering the host cell involves transfecting, transforming or transducing the cells with a recombinant polynucleotide molecule, and/or otherwise altering (e.g., by homologous recombination and gene activation or fusion of a recombinant cell with a non-recombinant cell) to cause the host cell to express a desired recombinant protein. Methods and vectors for genetically engineering cells and/or cell lines to express a protein of interest are well known to those of skill in the art.

A host cell can be any prokaryotic cell (for example, *E. coli*) or eukaryotic cell (for example, yeast, insect, or animal cells (e.g., CHO cells)). Vector DNA can be introduced into prokaryotic or eukaryotic cells via conventional transformation or transfection techniques.

In one embodiment, the cell is a host cell. A host cell, when cultured under appropriate conditions, expresses the protein of interest that can be subsequently collected from the culture medium (if the host cell secretes it into the medium) or directly from the host cell producing it (if it is not secreted).

Cell cultures can be operated in a batch, fed batch, continuous, semi-continuous, and/or perfusion modes. Mammalian cells, such as CHO cells, may be cultured in bioreactors at a smaller scale of less than 100 ml to less than 1000 mls. Alternatively, larger scale bioreactors at 1000 mls to over 20,000 liters can be used. In one embodiment 1 liter to 2000 liters are used. In one embodiment the bioreactor is 10 liters to 2000 liters. In one embodiment the bioreactor is 10 liters to 100 liters. In one embodiment the bioreactor is 30 liters to 50 liters. In one embodiment the bioreactor is 30 liters to 2000 liters. In one embodiment the bioreactor is 100 liters to 2000 liters. In one embodiment the bioreactor is 500 liters to 2000 liters. In one embodiment the bioreactor is 1000 liters to 2000 liters. Larger scale cell cultures, such as for clinical and/or commercial scale biomanufacturing of protein therapeutics, may be maintained for weeks and even months, while the cells produce the desired protein(s). Bioreactors may comprise single use components.

Following culture in bioreactors, the resulting expressed recombinant protein of interest can then be harvested from the cell culture media. Methods for harvesting recombinant proteins from suspension cells are known in the art and include, but are not limited to, acid precipitation, accelerated sedimentation such as flocculation, separation using gravity, centrifugation, acoustic wave separation, filtration, including membrane filtration, ultrafilters, microfilters, tangential flow filters, alternative tangential flow, depth filters, and alluvial filtration filters. Recombinant proteins expressed by prokaryotes are retrieved inclusion bodies in the cytoplasm by redox folding processes known in the art.

The harvested recombinant protein of interest can be stored in surge tanks, holding tanks, bags, or other containers that are adapted to provide feed to a chromatography column skid. The harvested recombinant protein of interest may also be provided directly to a chromatography column skid as an eluate stream.

The harvested protein of interest is then purified, or partially purified, away from any impurities and/or contaminants, such as remaining cell culture media, cell extracts, cell debris, host cell proteins, bacteria, yeast, mycobacteria, viruses, endotoxins, DNA, RNA, product-related impurities such as homodimers, half antibodies, aggregates, antibody fragments and various combinations of antibody fragments, and light chain mis-assemblies, such as 2XLC, 3XLC, or 4XLC, high molecular weight (HMW) species, low molecular weight (LMW) species, deaminated species, and the like, using one or more unit operations.

Processes for the purification recombinant proteins of interest generally include unit operations encompassing one or more processes involved in capture, bulk and fine purification, virus reduction/inactivation, concentration, and/or formulation.

The term unit operation or operation as used herein refers to a functional step that can be performed as a part or component of a process for purifying a recombinant protein of interest from a liquid culture medium. Unit operations can also include holding or storing steps between processing steps. A single unit operation may be designed to accomplish multiple objectives in the same operation, such as capture and viral inactivation.

The concentration of the purified protein and buffer exchange into a desired formulation buffer for bulk storage of the drug substance can be accomplished by an ultrafiltration and diafiltration unit operation. The formulated drug product may be further subjected to sterile filtration to ensure the drug product is free of viable microorganisms and then subject to a fill/finish process where the drug product is introduced to an aseptic processing facility for filling into primary drug product containers or devices, which are then sealed, labeled and packaged for shipment and distribution.

Certain embodiments described herein can utilize logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

Although the systems, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

EXAMPLES

Example 1. Semi-Continuous Process with Two-Column Cycling for Capture, Automated Bolus Virus Inactivation, and Connected Flow-Through Polishing and Virus Filtration The Experiment describes a semi-continuous downstream purification process that uses a two-column cycling process for capture chromatography, see FIG. 3, followed by bolus virus inactivation followed by a connected flow-through polish chromatography and virus filtration process.

A perfusion cell culture expressing a recombinant monoclonal antibody (mAb A) was brought to a desired viable cell density steady state and the harvested cell culture fluid (HCCF) was collected into a surge vessel (disposable, pre-sterilized bag) prior to being subjected to an affinity chromatography unit operation.

The affinity chromatography unit operation comprised two independent Protein A chromatography skids, "Column 1" and "Column 2". Each skid was equipped with a 500 mL, 8×10 cm column containing MABSELECT SURE™ Protein A resin (Cytiva, Marlborough, MA), connected to an ÄKTA™ Pure Protein Purification System (Cytiva). The flow paths of the ÄKTA™ injection and column valves were modified to enable the parallel column cycling. The Protein A affinity chromatography columns were cycled in parallel, with no column connectivity during loading (no column overloading), by using alternating cycles to overlap the processing. In this capture column cycling strategy, the longest phase of the cycling, the loading step, used a dedicated pump (Pump 1). The remaining steps (wash-equilibration) were executed using a separate second pump (Pump 2), thus enabling overlapping the column cycling operations between the columns on the different skids, without creating a column connectivity.

For Run #1, Column 1 was equilibrated with Tris buffer (pH 7.4) at the completion of its last run. A central processor directed loading of harvested cell culture fluid (HCCF) onto Column 1 at a rate of 5 to 7.5 minutes residence time to a loading concentration of 35 g/L using Pump 1. To maintain the independence of each column, the HCCF feed entered the injection valve of the ÄKTA™ system through a common HCCF feed port but exited through a port directly connected to Column 1. Once loading was complete, what remained of the feed exited Column 1 and entered the column valve of the ÄKTA system through a port directly connected to only Column 1 and then exited through a common waste port, See FIG. 11.

Upon completion of loading of the HCCF feed onto Column 1, Pump 1 was signaled to disengage, and Pump 2 was signaled to engage. Column 1 was then washed, eluted, regenerated, flushed and re-equilibrated.

The buffers entered through a common buffer feed port on the injection valve of the ÄKTA™ system and exited through a port connected directly to Column 1 only. Upon exiting Column 1, the fluid entered the column valve through a port directly connected to Column 1 only and exited at a common exit port that was connected to a UV detector and outlet valve, see FIG. 12. The flush buffer and the equilibration buffer were the same, allowing for re-equilibration of the column in preparation for the next loading cycle.

The length of time required for the loading cycle determined the length of time during which the wash through equilibration steps would be cycled. The flow rates of the processing steps were determined, allowing for a time gap if needed, to enable the parallel processing of Columns 1 and 2.

In parallel, once Column 1 completed HCCF loading, Pump 1 was signaled to begin HCCF loading of Column 2. The HCCF feedstock entered the injection valve through the common HCCF feed port on the ÄKTA™ system but exited through a port directly connected to Column 2 only. Once Column 2 loading was complete, the eluate exited Column 2 to the column valve at a port directly connected to Column 2 only and exited through a common waste port.

Once Column 2 completed HCCF loading, Pump 1 was signaled to disengage loading Column 2 and to begin loading Column 1 again. Pump 2 was signaled to engage, and Column 2 was washed, eluted, regenerated, flushed and equilibrated. The buffers entered the injection valve through the common buffer feed port on the ÄKTA™ system and exited through a port directly connected to Column 2 only. Upon completion of each step, the eluate from Column 2 entered the column valve through a port directly connected to Column 2 only and exited the column valve at the common exit port connected to a UV detector and outlet valve.

For both Columns 1 and 2, elution of mAb A from the Protein A resin was performed using a low pH buffer, 100 mM formate at pH 3.4, into a common surge vessel. The volume of the elution was 3.1 CVs, resulting in a Protein A elution pool pH of 3.58. The pH and volume of elution was selected to achieve a capture pool pH of 3.6±0.1. This enabled the capture pool to be at the desired virus inactivation conditions immediately following elution.

After holding the Protein A capture pool at the target pH (3.6±0.1) for at least 15 minutes, not longer than up to 2 hours, the pool was transferred to a disposable bag and neutralized in-line using a static mixer with a bolus addition of neutralizing buffer to a target pH of 5.0. The neutralizing buffer, 170 mM Acetate, 115 mM Tris Base pH 8.5, was added in a ratio of 1-part virus inactivated pool to 0.42-part neutralization buffer. The neutralization buffer was designed to use a volume of addition which could be easily controlled during in-line addition and contained a background buffering agent (acetate) which buffered at the target pH. The resulting neutralized virus inactivation pool (NVIP) had a pH of 5.1.

The cycles of Protein A capture/virus inactivation/neutralization of HCCF containing mAb A were continued for 5 days and were combined into a single NVIP pool. This process was repeated for a total of 4 times over 20 days, resulting in 4 separate NVIP pools.

The pools were then filtered through a depth filter, MILLISTACK™ A1HC (MilliporeSigma, Burlington, MA). The filter was flushed per the vendor recommendation prior to use. The depth filter was loaded at 111 LMH and the permeate collected in a surge vessel. Once 5 liters of filtered virus inactivation pool (FVIP) was collected, the flow-through polishing and virus filtration steps were initiated.

The surge vessel containing the FVIP was connected to another ÄKTA™ Pure Protein Purification System (Cytiva) that contained two connected columns, an anion exchange chromatography column (AEX), 8×10 cm, CAPTO™ Q (Cytiva) directly connected to a cation exchange chromatography column (CEX), 8×10 cm, ESHMUNO® CPX (MilliporeSigma), followed by a virus filter (FIG. 13). The AEX-CEX connected column was loaded at an 8.3 minute residence time to a loading density of 290 g/Liter resin. The dual column output was diverted directly into a virus filter operation, a pre-filter (MILLISTACK™ A1HC, MilliporeSigma) followed by a VIRESOLVE Pro virus filter (VPro, MilliporeSigma). The virus filter (VF) was loaded at a flux of 16 LMH and the ratio of prefilter to virus filter area was 1:4. The VF pool was then collected and characterized for product quality. Each of the 4 NVIP pools were similarly processed.

Further processing and formulation of the VF pools can be performed using known methods for ultrafiltration and diafiltration (UF/DF) followed by polysorbate addition and drug substance fill (DS Fill) or connected UF/DF and DS Fill operations enabling a completely continuous drug substance process.

A second Run (Run #2), was performed using mAb A as described above. In both runs, the NVIP pools were collected every five days and then processed through the depth filter/polishing/virus filtration operations. This process was repeated over 20 days, resulting in 4 separate NVIP and VF pools as described for Run #1. For Run #2, the connected AEX/CEX columns were loaded to 600 g/liter resin at residence time of 8.3 minutes, 90 LMH.

The product quality for the neutralized virus inactivation pool and virus filtration pools for Run #1 and Run #2 are shown below in Table 1. The product quality was consistent with a robust single affinity column mAb process, demonstrating clearance and control of critical impurities using the parallel processing system.

TABLE 1

Product Quality Attributes for NVIP and VF pools from Runs 1 and 2

| | | Product Quality Attribute | | | |
|---|---|---|---|---|---|
| Run and Sample Details | | HMW (%) | Leached Protein A (ppm) | DNA (ppb) | Host Cell Protein (ppm) |
| Run #1 | NVIP Pool #1 | 3.1 | NT | NT | 214 |
| | NVIP Pool #2 | 3.3 | NT | NT | 213 |
| | NVIP Pool #3 | 3.2 | NT | NT | 278 |
| | NVIP Pool #4 | 3.4 | NT | NT | 310 |
| | VF Pool #1 | 0.7 | 0.42 | <6.7 | <1 |
| | VF Pool #2 | 0.7 | 0.38 | <6.8 | <1 |
| | VF Pool #3 | 0.7 | <0.25 | <6.6 | <1 |
| | VF Pool #4 | 0.7 | 0.48 | <7.6 | <2 |
| Run #2 | NVIP Pool #1 | 4.7 | 5.9 | 5.9 | 598 |
| | NVIP Pool #2 | 3.8 | 3.6 | 7.3 | 308 |
| | NVIP Pool #3 | 5.7 | 3.9 | <2.6 | 201 |
| | NVIP Pool #4 | 3.2 | 3.6 | 5.0 | 79 |
| | VF Pool #1 | 0.9 | NT | NT | 1 |
| | VF Pool #2 | 0.9 | NT | NT | <1 |
| | VF Pool #3 | 0.8 | NT | NT | <2 |
| | VF Pool #4 | 0.8 | NT | NT | <1 |

NT = Not Tested
NVIP = neutralized virus inactivated pool
VF = virus filtration

In addition to the critical impurities, the NVIP pools were characterized for charge variants. The results are shown in Table 2 below. The charge variants were consistent across the four pools in each run and met product quality expectations.

TABLE 2

Charge variants in neutralized virus inactivation pools for Runs 1 and 2

| | | Charge Variants | | |
|---|---|---|---|---|
| Run and Sample Details | | Main Peak (%) | Acidic Variants (%) | Basic Variants (%) |
| Run #1 | NVIP Pool #1 | 80.1 | 3.3 | 16.6 |
| | NVIP Pool #2 | 79.4 | 3.3 | 17.3 |
| | NVIP Pool #3 | 78.8 | 3.5 | 17.7 |
| | NVIP Pool #4 | 79.0 | 3.7 | 17.3 |
| Run #2 | NVIP Pool #1 | 81.7 | 3.7 | 14.6 |
| | NVIP Pool #2 | 81.8 | 4.0 | 14.2 |
| | NVIP Pool #3 | 81.0 | 4.9 | 14.1 |
| | NVIP Pool #4 | 80.6 | 3.7 | 14.8 |

Example 2. Semi-Continuous Process with Two-Column Cycling for Protein A Affinity Chromatography, Automated Bolus Virus Inactivation/Neutralization, Two-Column Cycling CEX Polishing Chromatography and Flow Through Mixed-Mode Chromatography The process described in Example 1 was modified to use parallel processing for one polish chromatography operation. This process comprised a two-column cycling cation exchange chromatography (CEX) unit operation in bind and elute mode in combination with a single column mixed mode chromatography (MM) unit operation, in flow through mode. The process was tested with a bispecific antibody, Bispecific A.

Bispecific A was initially processed using an affinity chromatography unit operation comprising two parallel Protein A chromatography columns (MABSELECT™ SURE, Cytiva) as described in Example 1. The Protein A columns were eluted using a 100 mM formate buffer at pH 3.4. This was repeated and resulted in two Protein A elution pools, one at pH 3.65 and one at pH 3.60. Both Protein A elution pools were at the target pH, so the elution pools were held for ≥30 minutes for virus inactivation. The virus inactivated pools were then neutralized using an in-line static mixer with a bolus addition of neutralizing buffer. The neutralizing buffer (170 mM Acetate, 115 mM Tris Base pH 8.5) was added at a ratio of 1-part virus inactivated pool to 0.23 part neutralization buffer. The resulting neutralized virus inactivation pool (NVIP) had a pH of 4.5. The NVIP pool was further processed through a depth filter (MILLISTACK A1HC, MilliporeSigma) to generate a filtered neutralized virus inactivated pool (FVIP).

The FVIP was processed using a two-column cation exchange unit operation as exemplified in FIG. 5. The CEX chromatography operation comprised two CEX chromatography skids "Column 1" and "Column 2". Each skid contained a 500 mL, 8×10 cm, ESHMUNO® CPX CEX chromatography column (MilliporeSigma) connected to an ÄKTA™ Pure Protein Purification System (Cytiva). The CEX chromatography columns were cycled in parallel, with no column connectivity during loading (no column overloading), by using alternating cycles to overlap the processing. Unlike the parallel Protein A cycling strategy described in Example 1 where the longest phase was the loading step, in this CEX chromatography parallel cycling strategy the longest phase of the cycle was the elution step, which used two dedicated pumps (Pumps 2A and 2B) to control an elution gradient. The production process steps (regeneration-equilibration) were executed using a separate pump (Pump 1), which enabled overlapping the column cycling operations between the two parallel columns on the different skids, without creating a column connectivity. The flow paths of the ÄKTA injection and column valves were modified to enable the parallel column cycling.

CEX Column 1 was equilibrated followed by loading the filtered virus inactivation pool (FVIP) at a rate of 150 cm/h linear velocity to a loading density of 5-20 g/L using Pump 1. The flow rate was chosen to maintain the timing of the parallel cycling between the columns, providing a time gap to keep the parallel column processes in sync. To maintain the independence of each column, the FVIP feed entered the injection valve of the ÄKTA™ system through a common FVIP feed port and exited through a port directly connected only to Column 1. Once loading was complete, what remained of the waste exited Column 1 and entered the column valve of the ÄKTA™ system through a port directly connected to only Column 1 and then exited through a common port.

Upon completion of loading of the FVIP feed onto Column 1, the column was then washed. The wash buffer entered through a common buffer feed port on the injection valve of the ÄKTA™ system and exited through a port connected directly to Column 1 only. Upon exiting Column 1, the fluid entered the column valve through a port directly connected to Column 1 only and exited at a common exit port that was connected a common waste port.

Once the wash step was completed, Pump 1 was signaled to disengage and Pumps 2A and 2B were signaled to begin the gradient elution. Bispecific A was eluted from the CEX columns by a sodium chloride gradient.

In parallel, when Column 1 began the elution step, Pump 1 was signaled to begin the production processing steps for Column 2. While Column 1 was being eluted, Column 2 was loaded and washed. To maintain the independence of each column using a single valve, neither column used the same common ports at the same time and the ports entering and exiting Column 1 or Column 2 were directly to that column.

Once the eluate fractions were collected from Column 1, Pumps 2A and 2B were signaled to disengage. Pump 1 was signaled to once again begin the production processing steps for Column 1.

Pumps 2A and 2B were signaled to begin elution of Column 2. Following the completion of the elution for Column 2, Pumps 2A and 2B were signaled to disengage, and the Pump 1 was signaled to once again begin the production processing steps for Column 2 (regeneration through washing) and Pumps 2A and 2B were engaged to elute Column 1.

The CEX elution pools from Columns 1 and 2 were then loaded on to an equilibrated mixed mode chromatography column (MMC) (Capto™ Adhere, Cytiva) in flow-through mode.

The MMC flow-through pool was collected, passed through a virus removal filter, followed by concentration and formulation using ultrafiltration and diafiltration (UF/DF) to the final drug substance formulation.

The product quality and process performance were as expected. The key results are shown in Table 3 below.

TABLE 3

Product quality for parallel CEX chromatography run.

| Process Pool | HMW (%) |
|---|---|
| Filter Virus Inactivation Pool (FVIP) | 27%-34% |
| Cation Exchange Pool (CEX) | 3.5%-4.0% |
| Flow-through Mixed Mode (MMC) | 1.9% |

Example 3. Low pH Viral Inactivation in Protein A Pool

The experiment describes the development of suitable Protein A elution conditions to achieve low pH virus inactivation without the need for an additional conditioning step following elution. Various elution buffer formulations were tested for the purpose of achieving a Protein A elution pool with a pH of 3.6±0.1. The elution pool volume and elution buffer strength (buffer concentration) typically determine the pH of the final collected Protein A elution pool.

The elution buffer concentration and pH required to enable a final pool pH of 3.6±0.1 was determined via screening experiments using a formate elution buffer at concentrations of 50, 75, 100, 125, and 150 mM at a pH of 3.2, 3.4, and 3.6. Mab A was loaded at 36 g/L on to a Protein A resin (MABSELECT SURE, Cytiva) using an ÄKTA™ Avant 150 (Cytiva) system and then eluted according to the buffer conditions in Table 4 and fractions were collected across the complete elution. The fractions were mixed to form pseudo pools representing various elution pool collection volumes. The pseudo pool pH was then measured to determine the effect of elution buffer pH, concentration, and collected volume on achieving a target pool pH of 3.6±0.1 and is shown in Table 4.

TABLE 4

Protein A Buffer pH and concentration enabling a Protein A pool at pH 3.6.

| Elution Buffer Concentration (mM) | Elution Buffer pH | Collected Elution Volumes (CV) | Resulting Elution Pool pH |
|---|---|---|---|
| 100 | 3.4 | 2.75 | 3.64 |
| 100 | 3.4 | 3 | 3.63 |
| 100 | 3.4 | 3.25 | 3.62 |
| 100 | 3.4 | 3.5 | 3.61 |
| 100 | 3.4 | 3.75 | 3.6 |
| 100 | 3.4 | 4 | 3.6 |
| 100 | 3.4 | 4.25 | 3.59 |
| 100 | 3.4 | 3.1 | 3.58 |
| 100 | 3.3 | 3.21 | 3.6 |
| 100 | 3.35 | 3.35 | 3.6 |
| 100 | 3.4 | 3.5 | 3.6 |
| 100 | 3.45 | 3.67 | 3.6 |
| 100 | 3.5 | 3.87 | 3.6 |
| 50 | 3.3 | 6.42 | 3.6 |
| 50 | 3.35 | 6.69 | 3.6 |
| 50 | 3.4 | 7 | 3.6 |
| 50 | 3.45 | 7.34 | 3.6 |
| 50 | 3.5 | 7.73 | 3.6 |
| 75 | 3.3 | 4.28 | 3.6 |
| 75 | 3.35 | 4.46 | 3.6 |
| 75 | 3.4 | 4.67 | 3.6 |
| 75 | 3.45 | 4.9 | 3.6 |
| 75 | 3.5 | 5.15 | 3.6 |
| 125 | 3.3 | 2.57 | 3.6 |
| 125 | 3.35 | 2.68 | 3.6 |
| 125 | 3.4 | 2.8 | 3.6 |
| 125 | 3.45 | 2.94 | 3.6 |
| 125 | 3.5 | 3.09 | 3.6 |
| 150 | 3.3 | 2.14 | 3.6 |
| 150 | 3.35 | 2.23 | 3.6 |
| 150 | 3.4 | 2.33 | 3.6 |
| 150 | 3.45 | 2.45 | 3.6 |
| 150 | 3.5 | 2.58 | 3.6 |

Figure 12:
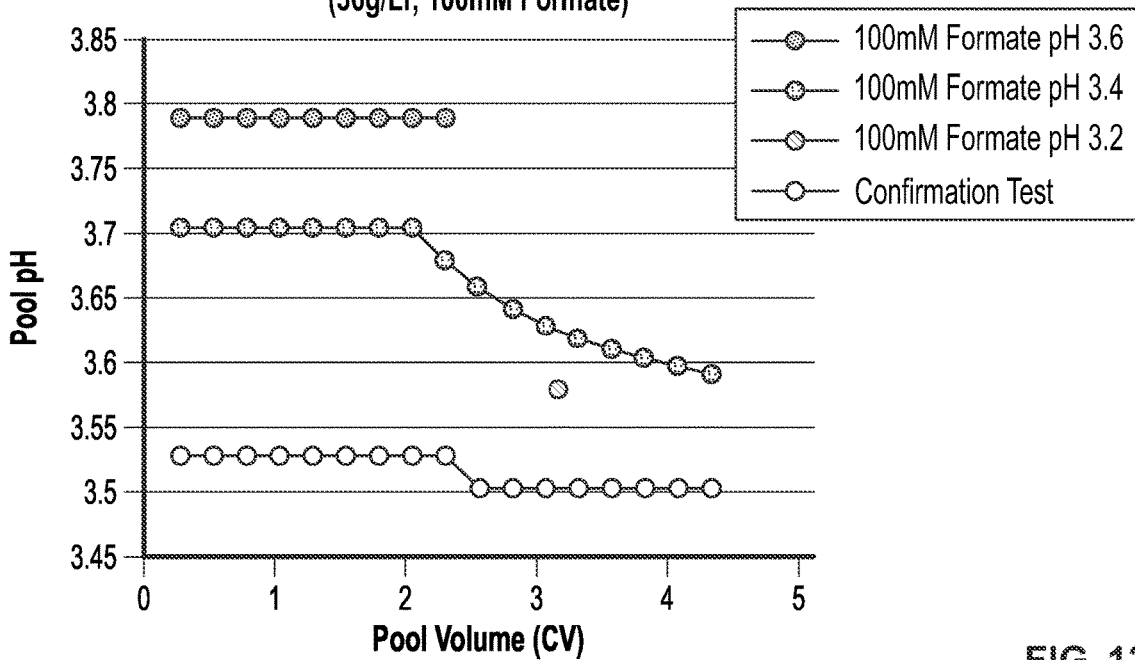
FIG. 12 is a graph showing a Protein A elution pool pH vs. collected elution volume.

The experiment was repeated, the Protein A column was loaded at 36 g/L MabA and eluting with a 100 mM formate elution buffer at pH 3.4, collecting a total of 3.2 column volumes (CVs), FIG. 12. This represented approximately 2.5 CVs of additional elution buffer than the minimum required to elute the recombinant protein of interest (~1 CV). A final pool pH of 3.6±0.1 was achieved.

It was found that there is an interdependence between the elution buffer pH, elution buffer concentration, and pool collection volume. At a target elution buffer concentration of 100 mM, a buffer pH range of pH 3.3 to pH 3.5 and Protein A pool collection volume range from 2.75 to 4.25 CV will result in the target pH range of 3.6±0.1. Table 4 shows that the parameters Protein A pool volumes collected, neutralization buffer required, and pool protein concentration, could be optimized by varying the Protein A elution buffer pH and concentration, enabling pool volumes up to 7.7 CV and as low as 2.1 CV.

Example 4. Development of mAb Virus Inactivation Bolus Neutralization

Following low pH incubation of an affinity chromatography elution pool, the pH of the pool is typically adjusted to be more compatible with any following downstream polish chromatography steps. The typical neutralization process makes use of a high concentration buffer, such as 1 M Tris, to titrate the pool to the target pH. A high concentration buffer is utilized to minimize the pool volume expansion (minimize the titrant addition) to enable facility fit for large scale production. However, for smaller volume, more intensified production processes, the use of a high concentration buffer (>0.5 M) makes bolus addition of titrant more difficult to control due to the smaller volumes of titrant required. This experiment describes the development of a bolus addition of an intermediate concentration neutralizing buffer to a viral inactivated Protein A elution pool.

Neutralizing buffer formulations that contained two components: a buffering component that buffers at the appropriate pH and a titrant component that adjusts the pH to the target value were tested. Various concentrations of buffering and titrating components were tested to identify those that resulted in pool conductivities of ≤10 mS/cm and pool volume increases of 50% or less, which were more useful for smaller scale manufacturing processes (data not shown). The combination of sodium acetate (NaOAc) and Tris Base met those requirements and were further tested.

Neutralizing buffer formulations containing sodium acetate and Tris Base in a bolus amount were added to two different mAb A concentrations (35 g/Lr and 17.5 g/Lr), and the resulting pool pH was measured. This experiment mimicked an in-line static mixer controlling the ratio of titrant via the ratio of pool vs. titrate flow rate. The tested conditions and results of the bolus neutralization experiments are shown in Table 5.

TABLE 5

Determination of Titrant Volume to Neutralize Virus Inactivation Pool to pH 5.0 ± 0.1

| Titrant Description | Pool Description | Titrant Volume/ Pool Volume (mL/L) | Total Titrant Volume (Vol % Pool) | Resulting Pool pH | Pool Conductivity (mS/cm) |
|---|---|---|---|---|---|
| 0.238M NaOAc, 0.185M Tris Base | ProA Pool 35 g/Lr Load Eluted w/Formate pH 3.4 | 0 | 0 | 3.57 | |
| | | 67 | 7 | 3.95 | |
| | | 133 | 13 | 4.34 | |
| | | 167 | 17 | 4.53 | |
| | | 200 | 20 | 4.69 | |
| | | 233 | 23 | 4.86 | |
| | | 267 | 27 | 5.02 | |
| | | 280 | 28 | 5.08 | 8.2 |
| | ProA Pool 17.5 g/Lr Load Eluted w/Formate pH 3.4 | 0 | 0 | 3.53 | |
| | | 67 | 7 | 3.88 | |
| | | 133 | 13 | 4.24 | |
| | | 200 | 20 | 4.57 | |
| | | 233 | 23 | 4.75 | |
| | | 267 | 27 | 4.9 | |
| | | 300 | 30 | 5.04 | |
| | | 313 | 31 | 5.11 | 8.2 |
| 0.17M NaOAc, 0.115M Tris Base | ProA Pool 17.5 g/Lr Load Eluted w/Formate pH 3.4 | 0 | 0 | 3.54 | |
| | | 67 | 7 | 3.77 | |
| | | 133 | 13 | 4.01 | |
| | | 200 | 20 | 4.24 | |
| | | 267 | 27 | 4.47 | |
| | | 333 | 33 | 4.67 | |
| | | 400 | 40 | 4.85 | |
| | | 420 | 42 | 4.9 | |
| | | 460 | 46 | 5 | |
| | | 500 | 50 | 5.1 | 7.6 |
| | ProA Pool 35 g/Lr Load Eluted w/Formate pH 3.4 | 0 | 0 | 3.59 | |
| | | 45 | 5 | 3.75 | |
| | | 170 | 17 | 4.21 | |
| | | 295 | 30 | 4.65 | |
| | | 358 | 36 | 4.82 | |
| | | 420 | 42 | 5 | |
| | | 451 | 45 | 5.08 | 7.7 |

The preferred titrant formulation provided a pool pH of 5.0±0.1 with conductivities 10 mS/cm for both 17 g/Lr and 35 g/Lr Protein A loaded pools and resulted in a pool volume increase of ≤50%.

Example 5. Small-Scale Connected Dual Column Polish and Viral Filtration Operations This experiment provides a scaled-down dual column, connected polishing and virus filtration operation, tested at lab scale. Table 6 describes the unit operations, scaling, and process parameters. The process was tested using mAb A in a representative filtered virus inactivation pool (FVIP). The process was executed using 100 mM Sodium Acetate, pH 5.0, ~5 mS/cmas for the equilibration and wash buffers. The virus pre-filter (VIRESOLVE® (VPF) MilliporeSigma) and virus filter (VIRESOLVE® Pro (VPro), MilliporeSigma) were flushed with water prior connecting in-line with a connected CAPTO Q Anion Exchange (AEX) column and an Eshmuno CPX Cation Exchange (CEX) column (both from Cytiva).

The connected chromatography columns and virus pre-filter/virus filter were equilibrated together in-line using a modified ÄKTA™ AVANT 150 periodic countercurrent chromatography (PCC) system (Cytiva). The pressure for the virus filter remained under 10 psi for the entire unit operation. Results of two test runs (Run #1 and Run #2) of the dual column, connected polishing and virus filtration are shown in Table 7. The both test runs showed good removal of high molecular weight species (HMW) and host cell proteins (CHOP) with acceptable overall step yield (~80%).

TABLE 6

| Column conditions | | | |
|---|---|---|---|
| Unit Operation | Parameter | Lab Scale | Process Scale |
| CAPTO Q Anion Exchange (AEX) Flow Through Chromatography | Column dimensions (cm) | 0.66 × 6.7 | 8 × 10 |
| | Column Volume (mL) | 2.3 | 500 |
| | Flow rate (mL/min) | 0.46 | 100 |
| | Residence time (min) | 5.0 | 5.0 |
| | Loading level (g/Lr) | 600 | 600 |
| ESHMUNO CPX Cation Exchange (CEX) Frontal Chromatography | Column dimensions (cm) | 0.66 × 6.7 | 8 × 10 |
| | Column Volume (mL) | 2.3 | 500 |
| | Flow rate (mL/min) | 0.46 | 100 |

TABLE 6-continued

| Unit Operation | Parameter | Lab Scale | Process Scale |
|---|---|---|---|
| | | Column conditions | |
| | Residence time (min) | 5.0 | 5.0 |
| | Loading level (g/Lr) | 600 | 600 |
| VPF/VPro | Pre-Filter Device | OptiScale-40 | POD |
| Purpose: Viral clearance | VPF Membrane area (cm²) | 5 | 1100 |
| | Virus Filter Device | Micro | Modus 1.2 |
| | VF Membrane area (cm²) | 3.1 | 700 |
| | VPro Flux (LMH) | 89 | 86 |

TABLE 7

Results of Lab Scale Dual Column, Connected
Polishing and Virus Filtration Tests

| Sample ID | Step Yield (%) | QSEC % HMW | rCE % LC + HC | CHOP (ppm) |
|---|---|---|---|---|
| Load | — | 3.8 | 96.5 | 67 |
| FVIP Pool | 80.5 | 1.2 | 97.6 | 5 |
| mAb A Pool Run #1 AEX → CEX → VF | 82.6 | 0.9 | NT | ≤7 |
| mAb A Pool Run #2 AEX → CEX → VF | 84.1 | ≤1.0 | ≥97 | ≤24 |

NT = Not Tested

A third lab scale test run (Run #3) was executed using mAb A to characterize additional impurity removal using the same conditions described above using a mAb A neutralized virus inactivation pool (NVIP). The results of run #3 are shown in Table 7. The process showed clearance of HMW, CHOP, DNA, and leached Protein A as expected. The process yield was also in the expected range.

TABLE 8

Lab scale test run #3 characterizing additional impurity removal

| Sample ID | Step Yield (%) | HMW (%) | CHOP (ppm) | DNA (ppb) | Leached Protein A (ppm) |
|---|---|---|---|---|---|
| NVIP | — | 5.0 | 228 | 5.3 | 5.6 |
| mAb A Pool Run #3 AEX → CEX → VF | 82 | 0.8 | 17 | <1.9 | 2.1 |

In addition, virus removal testing was executed on the AEX and CEX columns were run independently using the conditions described above, to characterize the viral clearance capability of the AEX and CEX steps. The columns were spiked with Xenotropic Murine Leukemia Virus (XMuLV) and loaded to 800 g/Lr. The AEX column produced a product yield of 98% and an XMuLV clearance of 3.4 Log. The CEX column produced a product yield of 84% and an XMuLV clearance of 4.0 Log.

Example 6. Connected, Dual Column Flow-Through Polishing Using Bispecific B

A Protein A capture pool was generated in accordance with the procedure described in Example 2 using bispecific antibody Bispecific B, with the exception that the elution was performed at pH 3.9. The virus inactivation was performed by titration using acetic acid to pH 3.6, followed by titration with Tris base to pH 5.0 and holding for ~1 hour.

The neutralized virus inactivation pool was filtered using a depth filter (Millistak A1HC, MilliporeSigma) and the FVIP was collected as a single pool and conditioned to 5 mM NaCl.

The conditioned FVIP pool was used to screen for optimum conditions for a two-column connected, flow-through polishing step comprising a cation exchange (CEX) chromatography column as the first column (SP-ImpRes HiScreen 4.7 mL, Cytiva), followed by a mixed mode (MMC) chromatography column (Capto Adhere HiScreen 4.7 mL, GE Healthcare). Both columns were equilibrated with 100 mM acetate, pH 5.0, at 150 mM and 175 mM NaCl. All the process steps were executed at 150 cm/hr. For ease of sampling, the columns were operated independently, the CEX eluate pool was characterized prior to loading on the MMC column. Bispecific B was loaded onto CEX and MMC at 75 g/L and washed with equilibration buffer.

The process conditions and product quality results are shown in Table 8. The two polishing steps were designed to work together to deliver a consistent result. At 150 mM NaCl, the CEX column removed more high molecular weight species (HMW), with as expected lower yield, and the MMC column further removed HMW with higher yield. Conversely, at 175 mM NaCl, the CEX column removed less HMW with a high yield and the MMC column removed more HMW with lower yield. The overall yield for the combined, connected polishing would be similar ~55% with a similar resulting pool purity ~1.6% HMW.

TABLE 9

Process conditions and product quality
for connected, dual column polishing

| Parameter | 150 mM NaCl pH 5.0 | 175 mM NaCl pH 5.0 |
|---|---|---|
| Load (FVIP) HMW (%) | 25.7 | 25.9 |
| CEX Yield (%) | 65 | 82 |
| CEX HMW (%) | 4.7 | 12.1 |
| MMC Yield (%) | 88 | 67 |
| MMC HMW (%) | 1.6 | 1.6 |
| Overall Polishing Step Yield (%) [CEX yield × MCC yield] | 57 | 55 |

What is claimed is:

1. A continuous parallel chromatography system, the system comprising:
a plurality of chromatography column skids having no flow path between or connecting the plurality of chromatography column skids to one another, each chromatography column skid suitable for independent batch processing and comprising:
a chromatography column;
an inlet selectively coupled to an upstream source;

at least one pump;

at least one filter; and an outlet sensor;

a control circuit configured to control the operation of the plurality of chromatography column skids through one or more full cycles of a chromatography process, each full cycle including a long step and a plurality of shorter steps, each of the plurality of shorter steps having a processing time shorter than or equal to a processing time of the long step, wherein the control circuit is configured to:

receive a synchronization signal associated with a first one of the plurality of chromatography column skids that the long step is complete; and in response to reception of the synchronization signal, direct operation of a second one of the plurality of chromatography column skids to commence operation of the long step.

2. The system of claim 1, wherein the control circuit is further configured to direct operation of the plurality of shorter steps on the first one of the plurality of chromatography column skids to complete the full cycle of the chromatography process therefor after reception of the synchronization signal.

3. The system of claim 2, wherein the control circuit is further configured to:

receive a second synchronization signal associated with the second one of the plurality of chromatography column skids that the long step is complete; and in response to reception of the second synchronization signal, direct operation of the first one of the plurality of chromatography column skids to commence a second operation of the long step.

4. The system of claim 3, wherein the control circuit is further configured to direct operation of the plurality of shorter steps on the second one of the plurality of chromatography column skids to complete the full cycle of the chromatography process therefor after reception of the second synchronization signal.

5. The system of claim 1, wherein the long step comprises (a) an eluting step for the chromatography column, or (b) a loading step for the chromatography column.

6. The system of claim 5, wherein the plurality of shorter steps comprise two or more of: an equilibration step, a loading step, one or more washing steps, a regeneration step, or a flushing step.

7. The system of claim 6, wherein:

the first one of the plurality of chromatography column skids is configured to receive a feed of feedstock from the upstream source and send the synchronization signal to the control circuit indicating that a load of the feedstock in the chromatography column of the first one of the plurality of chromatography columns is complete; and in response to reception of the synchronization signal, the control circuit is configured to switch the feed of the feedstock from the upstream source to the second one of the plurality of chromatography column skids to perform the loading step for the chromatography column thereof.

8. The system of claim 7, wherein the control circuit is further configured to direct a feed of one or more processing feedstocks to the first one of the plurality of chromatography column skids to perform processing of the short steps on the loaded chromatography column thereof.

9. The system of claim 8, wherein, after completion of the processing of the short steps on the loaded chromatography column, the first one of the plurality of chromatography column skids is configured to await a generation of a second synchronization signal associated with the second chromatography column skid that the loading step for the chromatography column thereof is complete.

10. The system of claim 7, wherein (a) the feedstock comprises a protein, an antibody, a multispecific protein, a bispecific protein, or a bi-specific T cell engager, and/or (b) the upstream source of the feedstock comprises one of: a stream or pool of harvested cell culture fluid, an elution stream or pool from a capture chromatography column, a viral inactivated pool from a capture chromatography column, or a neutralized viral inactivated pool from a capture chromatography column.

11. The system of claim 1, wherein the chromatography columns of the plurality of chromatography skids comprise capture chromatography columns.

12. The system of claim 11, wherein the capture chromatography columns comprise one or more of:

(a) affinity chromatography columns, (b) size exclusion chromatography columns, (c) ion exchange chromatography columns, (d) hydrophobic interaction chromatography columns, (e) multi-modal chromatography columns, (f) hydroxyapatite chromatography columns, (g) immobilized metal affinity chromatography columns, (h) affinity chromatography columns consisting of (A) Protein A chromatography columns, (B) Protein G chromatography columns, or (C) Protein L chromatography columns, or (i) ion exchange chromatography columns consisting of (A) cation exchange chromatography columns or (B) anion exchange chromatography columns.

13. The system of claim 1, further comprising at least one of a viral filtration device and/or an ultrafiltration device fluidly connected downstream of the plurality of chromatography column skids.

14. The system of claim 1, wherein the control circuit comprises at least one of (a) a plurality of controllers of each of the plurality of chromatography column skids in communication with one another, or (b) a central controller in communication with each of the plurality of chromatography column skids.

15. The system of claim 1, wherein the one or more of the chromatography columns of the plurality of chromatography column skids comprise at least one of (a) a plurality of different sizes relative to one another, or (b) single-use chromatography columns.

16. The system of claim 1, further comprising one or more collection tanks fluidly coupled downstream of the plurality of chromatography column skids.

17. The system of claim 16, further comprising a downstream capture chromatography column.

18. The system of claim 17, wherein the downstream chromatography column comprises:

(a) an ion exchange chromatography column, (b) a hydrophobic interaction chromatography column, (c) a multi-modal chromatography column, (d) a hydroxyapatite chromatography column, (e) a cation exchange column, (f) an anion exchange column, or (g) a first downstream chromatography column and a second downstream chromatography column connected directly in series with the first downstream chromatography column, wherein the first and second downstream chromatography columns optionally comprise cation and/or anion exchange columns.

19. The system of claim 17, wherein the downstream chromatography column comprises a first downstream chromatography column; and further comprising a second downstream chromatography column; wherein the first and second downstream chromatography columns are disposed on first and second downstream chromatography column skids, respectively, the first and second downstream chromatography column skids each suitable for independent batch processing and comprising:

an inlet;

at least one pump;

at least one filter; and an outlet sensor.

20. The system of claim 19, wherein the control circuit is configured to control operation of the first and second downstream chromatography column skids through one or more full cycles of a downstream chromatography process, each full cycle including a long elution step and a plurality of shorter steps, each of the plurality of shorter steps having a processing time shorter than or equal to a processing time of the long elution step, wherein the control circuit is configured to:

receive a synchronization signal associated with the first downstream chromatography column skid that the long elution step is complete; and in response to reception of the synchronization signal, direct operation of the second chromatography column skid to commence operation of the long elution step.

* * * * *